US006974575B2

(12) United States Patent
Cao et al.

(10) Patent No.: US 6,974,575 B2
(45) Date of Patent: Dec. 13, 2005

(54) GENERATION OF TYPE I/TYPE II HYBRID FORM OF BOVINE VIRAL DIARRHEA VIRUS FOR USE AS VACCINE

(75) Inventors: Xuemei Cao, East Lyme, CT (US); Gabriele M. Zybarth, West Kingston, RI (US)

(73) Assignees: Pfizer Inc., New York, NY (US); Pfizer Products Inc., Groton, CT (US)

( * ) Notice: Subject to any disclaimer, the term of this patent is extended or adjusted under 35 U.S.C. 154(b) by 0 days.

(21) Appl. No.: 10/228,406

(22) Filed: Aug. 27, 2002

(65) Prior Publication Data

US 2003/0104612 A1 Jun. 5, 2003

Related U.S. Application Data

(60) Provisional application No. 60/315,445, filed on Aug. 28, 2001.

(51) Int. Cl.[7] .............................................. A61K 39/00

(52) U.S. Cl. ............................... 424/192.1; 424/205.1; 435/69.1

(58) Field of Search .......................... 424/192.1, 205.1, 424/204.1; 435/69.1, 6

(56) References Cited

U.S. PATENT DOCUMENTS 6,001,613 A * 12/1999 Donis et al. ............... 435/91.4

OTHER PUBLICATIONS

Ventzislav et al, Journal of Virology, Jan. 1997, vol. 71, No. 1, pp. 471–478.*

Donis R.O. et al., "Differences in Virus–Induced Polypeptides in Cells Infected by Cytopathic and Noncytopathic Biotypes of Bovine Virus Diarrhea–Mucosal Disease Virus", *Virology 158*:168–173 (1987).

Collett M.S. et al., "Molecular Cloning and Nucleotide Sequence of the Pestivirus Bovine Viral Diarrhea Virus", *Virology 165*:191–199 (1988).

Bolin S.R. et al., "Range of Viral Neutralizing Activity and Molecular Specificity of Antibodies Induced in Cattle by Inactivated Bovine Viral Diarrhea Virus Vaccines", *American Journal of Veterinary Research 51*(5):703–707 (1990).

Howard C.J. et al., "Immunity to Bovine Virus Diarrhea Virus in Calves: The Role of Different T–Cell Subpopulations Analysed by Specific Depletion In Vivo with Monoclonal Antibodies", *Veterinary Immunology and Immunopathology 32*:303–314 (1992).

Larsson B. et al., "Bovine Virus Diarrhoea Virus Induces In Vitro a Proliferative Response of Peripheral Blood Mononuclear Cells from Cattle Immunized by Infection", *Veterinary Microbiology 31*:317–325 (1992).

Wiskerchen M. et al., "Pestivirus Gene Expression: Protein p80 of Bovine Viral Diarrhea Virus is a Proteinase Involved in Polyprotein Processing", *Virology 184*:341–350 (1991).

Tillmann R. et al., "Processing of the Envelope Glycoproteins of Pestiviruses", *Journal of Virology 67*(6):3288–3294 (1993).

Elbers K. et al., "Processing in the Pestivirus E2–NS2 Region: Indentification of Proteins p7 and E2p7", *Journal of Virology 70*(6):4131–4135 (1996).

Tautz N. et al., "Serine Protease of Pestiviruses: Determination of Cleavage Sites", *Journal of Virology 71*(7):5415–5422 (1997).

Ernesto J.X. et al., "Bovine Viral Diarrhea Virus NS3 Serine Proteinase: Polyprotein Cleavage Sites, Cofactor Requirements, and Molecular Model of an Enzyme Essential for Pestivirus Replication", *Journal of Virology 71*(7):5312–5322 (1997).

Beer M. et al., "Cytotoxic T–Lymphocyte Responses in Cattle Infected with Bovine Viral Diarrhea Virus", *Veterinary Microbiology 58*:9–22 (1997).

Lambot M. et al., "Characterization of the Immune Response of Cattle Against Non–Cytopathic and Cytopathic Biotypes of Bovine Viral Diarrhoea Virus", *Journal of General Virology 78*:1041–1047 (1997).

* cited by examiner

*Primary Examiner*—Ali R. Salimi
(74) *Attorney, Agent, or Firm*—Scully, Scott, Murphy & Pressser

(57) ABSTRACT

The present invention provides genetically engineered type I/type II hybrid BVDV viruses. The hybrid viruses, as well as the hybrid viral genome, can be used in immunogenic compositions and vaccines for protecting cattle from BVDV infection.

7 Claims, 10 Drawing Sheets

Construction of plasmid pNADL890

```
Seq9pNADL890.txt
Position 1 is the first nucleotide of NADL890 genome.
The E2 region of 890 is 2 animo acids shorter than that from NADL.^
^
GTATACGAGAATTAGAAAAGGCACTCGTATACGTATTGGGCAATTAAAAATAATAATTAGGCCTAGG
GAACAAATCCCTCTCAGCGAAGGCCGAAAAGAGGCTAGCCATGCCCTTAGTAGGACTAGCATAATGA
GGGGGGTAGCAACAGTGGTGAGTTCGTTGGATGGCTTAAGCCCTGAGTACAGGGTAGTCGTCAGTGG
TTCGACGCCTTGGAATAAAGGTCTCGAGATGCCACGTGGACGAGGGCATGCCCAAAGCACATCTTAA
CCTGAGCGGGGGTCGCCCAGGTAAAAGCAGTTTTAACCGACTGTTACGAATACAGCCTGATAGGGTG
CTGCAGAGGCCCACTGTATTGCTACTAAAAATCTCTGCTGTACATGGCACATGGAGTTGATCACAAA
TGAACTTTTATACAAAACATACAAACAAAAACCCGTCGGGGTGGAGGAACCTGTTTATGATCAGGCA
GGTGATCCCTTATTTGGTGAAAGGGGAGCAGTCCACCCTCAATCGACGCTAAAGCTCCCACACAAGA
GAGGGGAACGCGATGTTCCAACCAACTTGGCATCCTTACCAAAAAGAGGTGACTGCAGGTCGGGTAA
TAGCAGAGGACCTGTGAGCGGGATCTACCTGAAGCCAGGGCCACTATTTTACCAGGACTATAAAGGT
CCCGTCTATCACAGGGCCCCGCTGGAGCTCTTTGAGGAGGGATCCATGTGTGAAACGACTAAACGGA
TAGGGAGAGTAACTGGAAGTGACGGAAAGCTGTACCACATTTATGTGTGTATAGATGGATGTATAAT
AATAAAAAGTGCCACGAGAAGTTACCAAAGGGTGTTCAGGTGGGTCCATAATAGGCTTGACTGCCCT
CTATGGGTCACAAGTTGCTCAGACACGAAAGAAGAGGGAGCAACAAAAAAGAAAACACAGAAACCCG
ACAGACTAGAAAGGGGGAAAATGAAAATAGTGCCCAAAGAATCTGAAAAAGACAGCAAAACTAAACC
TCCGGATGCTACAATAGTG
GTGGAAGGAGTCAAATACCAGGTGAGGAAGAAGGGAAAAACCAAGAGTAAAAACACTCAGGACGGCT
TGTACCATAACAAAAACAAACCTCAGGAATCACGCAAGAAACTGGAAAAAGCATTGTTGGCGTGGGC
AATAATAGCTATAGTTTTGTTTCAAGTTACAATGGGAGAAAACATAACACAGTGGAACCTACAAGAT
AATGGGACGGAAGGGATACAACGGGCAATGTTCCAAAGGGGTGTGAATAGAAGTTTACATGGAATCT
GGCCAGAGAAAATCTGTACTGGCGTCCCTTCCCATCTAGCCACCGATATAGAACTAAAAACAATTCA
TGGTATGATGGATGCAAGTGAGAAGACCAACTACACGTGTTGCAGACTTCAACGCCATGAGTGGAAC
AAGCATGGTTGGTGCAACTGGTACAATATTGAACCCTGGATTCTAGTCATGAATAGAACCCAAGCCA
ATCTCACTGAGGGACAACCACCAAGGGAGTGCGCAGTCACTTGTAGGTATGATAGGGCTAGTGACTT
AAACGTGGTAACACAAGCTAGAGATAGCCCCACACCCTTAACAGGTTGCAAGAAAGGAAAGAACTTC
TCCTTTGCAGGCATATTGATGCGGGGCCCCTGCAACTTTGAAATAGCTGCAAGTGATGTATTATTCA
AAGAACATGAACGCATTAGTATGTTCCAGGATACTACTCTTTACCTTGTTGACGGGTTGACCAACTC
CTTAGAAGGTGCCAGACAAGGAACCGCTAAACTGACAACCTGGTTAGGCAAGCAGCTCGGGATACTA
GGAAAAAAGTTGGAAAACAAGAGTAAGACGTGGTTTGGAGCATACGCTGCTTCCCCTTACTGTGATG
TGGATCGGAAGATCGGTTACGTCTGGTATACAAAAAACTGCACTCCAGCTTGCCTCCCAAGAAACAC
CAAGATAATAGGCCCCGGGAAGTTTGACACCAACGCCGAAGATGGCAAAATACTCCATGAGATGGGA
GGGCACCTCTCAGAATTTG
CCCTATTGTCCTTGGTGGTTCTGTCTGACTTTGCCCCAGAAACCGCGAGTGTCATCTACTTGGTTCT
ACATTTTGCGATCCCGCAAAGCCACGTTGATGTAGACACATGCGACAAGAACCAGCTGAATTTAACG
GTCGCAACTACAGTAGCAGAAGTCATACCAGGGACAGTGTGGAACCTAGGGAAGTATGTCTGCATAA
GACCGGACTGGTGGCCATATGAGACGACGACAGTCTTCGTCTTAGAGGAAGCAGGGCAAGTAATCAA
ATTGGGGCTAAGGGCCATCAGAGACTTAACTAGGATATGGAACGCTGCCACCACCACAGCTTTCCTA
ATCTTTTTAGTGAAAGCACTGAGGGGACAACTAATCCAAGGGCTATTGTGGCTGATGCTAATAACAG
GAGCTCAGGGCTTCCCTGAATGCAAGGAGGGCTTCCAATATGCCATATCGAAAGACAGAAAAATGGG
GTTATTGGGGCCAGAGAGCTTAACTACAACATGGCACCGTCCCACAAAAAAATTAGTGGACTCCATG
GTACAAGTATGGTGTGAAGGAAAAGACTTGAAAATATTAAAAACGTGCCCCAAGGAAGAGAGGTACC
TAGTGGCTGTGCACGAGAGAGCCCTATCAACCAGTGCTGAGTTTATGCCAATCAGTGATGGGACAAT
AGGCCCAGATGTGATAGATATGCCTGATGACTTTGAGTTTGGACTCTGCCCTTGTGACGCAAAACCA
GTGATAAAGGGCAAATTTAATGCCAGCTTACTGAATGGACCAGCTTTCCAGATGGTATGCCCACAGG
GGTGGACTGGTACAATAGAATGCACCCTGGCGAACCAAGACACCTTAGACACAACTGTGGTTAGGAC
ATACAGAAGAACTACTCCATTTCAGCGGAGAAAATGGTGCTCCTATGAAAAAATAATAGGGGAAGAT
ATCCATGAATGCATTCTGGGTGGAAACTGGACATGCATAACTGGTGACCATAGCAAGTTGAAAGACG
GACCTATCAAGAAATGTAA
GTGGTGTGGCTATGACTTCGTCAACTCAGAGGGACTGCCACACTACCCAATAGGTAAGTGCATGCTC
```

Seq9pNADL890.txt

ATCAATGAGAGTGGGTACAGGTATGTAGATGACACCTCTTGCGATAGGGGTGGTGTAGCCATAGTCC
CAACAGGCACCGTAAAGTGTAGAATAGGTGACGTCACGGTGCAGGTTGTCGCTTCTAATAATGATCT
GGGACCCATGCCCTGCAGCCCAGCTGAAGTGATAGCAAGTGAAGGACCAGTGGAAAAGACTGCATGC
ACATTTAACTATTCAAGGACACTACCCAATAAGTATTATGAGCCAAGGGACCGTTACTTCCAACAAT
ACATGCTAAAAGGGGAGTGGCAATATTGGTTTGACCTGGATCATGTAGACCACCACAAAGACTACTT
CTCAGAGTTCATAATCATAGCAGTGGTCGCCTTGTTGGGTGGCAGATATGTACTTTGGTTACTGGTT
ACATACATGGTCTTATCAGAACAGAAGGCCTTAGGGATTCAGTATGGATCAGGGGAAGTGGTGATGA
TGGGCAACTTGCTAACCCATAACAATATTGAAGTGGTGACATACTTCTTGCTGCTGTACCTACTGCT
GAGGGAGGAGAGCGTAAAGAAGTGGGTCTTACTCTTATACCACATCTTAGTGGTACACCCAATCAAA
TCTGTAATTGTGATCCTACTGATGATTGGGGATGTGGTAAAGGCCGATTCAGGGGGCCAAGAGTACT
TGGGGAAAATAGACCTCTGTTTTACAACAGTAGTACTAATCGTCATAGGTTTAATCATAGCCAGGCG
TGACCCAACTATAGTGCCACTGGTAACAATAATGGCAGCACTGAGGGTCACTGAACTGACCCACCAG
CCTGGAGTTGACATCGCTGTGGCGGTCATGACTATAACCCTACTGATGGTTAGCTATGTGACAGATT
ATTTTAGATATAAAAAATGGTTACAGTGCATTCTCAGCCTGGTATCTGGGGTGTTCTTGATAAGAAG
CCTAATATACCTAGGTAGA
ATCGAGATGCCAGAGGTAACTATCCCAAACTGGAGACCACTAACTTTAATACTATTATATTTGATCT
CAACAACAATTGTAACGAGGTGGAAGGTTGACGTGGCTGGCCTATTGTTGCAATGTGTGCCTATCTT
ATTGCTGGTCACAACCTTGTGGGCCGACTTCTTAACCCTAATACTGATCCTGCCTACCTATGAATTG
GTTAAATTATACTATCTGAAAACTGTTAGGACTGATATAGAAAGAAGTTGGCTAGGGGGGATAGACT
ATACAAGAGTTGACTCCATCTACGACGTTGATGAGAGTGGAGAGGGCGTATATCTTTTTCCATCAAG
GCAGAAAGCACAGGGGAATTTTTCTATACTCTTGCCCCTTATCAAAGCAACACTGATAAGTTGCGTC
AGCAGTAAATGGCAGCTAATATACATGAGTTACTTAACTTTGGACTTTATGTACTACATGCACAGGA
AAGTTATAGAAGAGATCTCAGGAGGTACCAACATAATATCCAGGTTAGTGGCAGCACTCATAGAGCT
GAACTGGTCCATGGAAGAAGAGGAGAGCAAAGGCTTAAAGAAGTTTTATCTATTGTCTGGAAGGTTG
AGAAACCTAATAATAAAACATAAGGTAAGGAATGAGACCGTGGCTTCTTGGTACGGGGAGGAGGAAG
TCTACGGTATGCCAAAGATCATGACTATAATCAAGGCCAGTACACTGAGTAAGAGCAGGCACTGCAT
AATATGCACTGTATGTGAGGGCCGAGAGTGGAAAGGTGGCACCTGCCCAAAATGTGGACGCCATGGG
AAGCCGATAACGTGTGGGATGTCGCTAGCAGATTTCGAAGAAAGACACTATAAAAGAATCTTTATAA
GGGAAGGCAACTTTGAGGGTATGTGCAGCCGATGCCAGGGAAAGCATAGGAGGTTTGAAATGGACCG
GGAACCTAAGAGTGCCAGATACTGTGCTGAGTGTAATAGGCTGCATCCTGCTGAGGAAGGTGACTTT
TGGGCAGAGTCGAGCATGT
TGGGCCTCAAAATCACCTACTTTGCGCTGATGGATGGAAAGGTGTATGATATCACAGAGTGGGCTGG
ATGCCAGCGTGTGGGAATCTCCCCAGATACCCACAGAGTCCCTTGTCACATCTCATTTGGTTCACGG
ATGCCTTTCAGGCAGGAATACAATGGCTTTGTACAATATACCGCTAGGGGGCAACTATTTCTGAGAA
ACTTGCCCGTACTGGCAACTAAAGTAAAAATGCTCATGGTAGGCAACCTTGGAGAAGAAATTGGTAA
TCTGGAACATCTTGGGTGGATCCTAAGGGGGCCTGCCGTGTGTAAGAAGATCACAGAGCACGAAAAA
TGCCACATTAATATACTGGATAAACTAACCGCATTTTTCGGGATCATGCCAAGGGGGACTACACCCA
GAGCCCCGGTGAGGTTCCCTACGAGCTTACTAAAAGTGAGGAGGGGTCTGGAGACTGGCTGGGCTTA
CACACACCAAGGCGGGATAAGTTCAGTCGACCATGTAACCGCCGGAAAAGATCTACTGGTCTGTGAC
AGCATGGGACGAACTAGAGTGGTTTGCCAAAGCAACAACAGGTTGACCGATGAGACAGAGTATGGCG
TCAAGACTGACTCAGGGTGCCCAGACGGTGCCAGATGTTATGTGTTAAATCCAGAGGCCGTTAACAT
ATCAGGATCCAAAGGGGCAGTCGTTCACCTCCAAAAGACAGGTGGAGAATTCACGTGTGTCACCGCA
TCAGGCACACCGGCTTTCTTCGACCTAAAAAACTTGAAAGGATGGTCAGGCTTGCCTATATTTGAAG
CCTCCAGCGGGAGGGTGGTTGGCAGAGTCAAAGTAGGGAAGAATGAAGAGTCTAAACCTACAAAAAT
AATGAGTGGAATCCAGACCGTCTCAAAAAACACAGCAGACCTGACCGAGATGGTCAAGAAGATAACC
AGCATGAACAGGGGAGACTTCAAGCAGATTACTTTGGCAACAGGGGCAGGCAAAACCACAGAACTCC
CAAAAGCAGTTATAGAGGA
GATAGGAAGACACAAGAGAGTATTAGTTCTTATACCATTAAGGGCAGCGGCAGAGTCAGTCTACCAG
TATATGAGATTGAAACACCCAAGCATCTCTTTTAACCTAAGGATAGGGGACATGAAAGAGGGGGACA
TGGCAACCGGGATAACCTATGCATCATACGGGTACTTCTGCCAAATGCCTCAACCAAAGCTCAGAGC
TGCTATGGTAGAATACTCATACATATTCTTAGATGAATACCATTGTGCCACTCCTGAACAACTGGCA
ATTATCGGGAAGATCCACAGATTTTCAGAGAGTATAAGGGTTGTCGCCATGACTGCCACGCCAGCAG

Seq9pNADL890.txt

```
GGTCGGTGACCACAACAGGTCAAAAGCACCCAATAGAGGAATTCATAGCCCCCGAGGTAATGAAAGG
GGAGGATCTTGGTAGTCAGTTCCTTGATATAGCAGGGTTAAAAATACCAGTGGATGAGATGAAAGGC
AATATGTTGGTTTTTGTACCAACGAGAAACATGGCAGTAGAGGTAGCAAAGAAGCTAAAAGCTAAGG
GCTATAACTCTGGATACTATTACAGTGGAGAGGATCCAGCCAATCTGAGAGTTGTGACATCACAATC
CCCCTATGTAATCGTGGCTACAAATGCTATTGAATCAGGAGTGACACTACCAGATTTGGACACGGTT
ATAGACACGGGGTTGAAATGTGAAAAGAGGGTGAGGGTATCATCAAAGATACCCTTCATCGTAACAG
GCCTTAAGAGGATGGCCGTGACTGTGGGTGAGCAGGCGCAGCGTAGGGGCAGAGTAGGTAGAGTGAA
ACCCGGGAGGTATTATAGGAGCCAGGAAACAGCAACAGGGTCAAAGGACTACCACTATGACCTCTTG
CAGGCACAAAGATACGGGATTGAGGATGGAATCAACGTGACGAAATCCTTTAGGGAGATGAATTACG
ATTGGAGCCTATACGAGGAGGACAGCCTACTAATAACCCAGCTGGAAATACTAAATAATCTACTCAT
CTCAGAAGACTTGCCAGCC
GCTGTTAAGAACATAATGGCCAGGACTGATCACCCAGAGCCAATCCAACTTGCATACAACAGCTATG
AAGTCCAGGTCCCGGTCCTATTCCCAAAAATAAGGAATGGAGAAGTCACAGACACCTACGAAAATTA
CTCGTTTCTAAATGCCAGAAAGTTAGGGGAGGATGTGCCCGTGTATATCTACGCTACTGAAGATGAG
GATCTGGCAGTTGACCTCTTAGGGCTAGACTGGCCTGATCCTGGGAACCAGCAGGTAGTGGAGACTG
GTAAAGCACTGAAGCAAGTGACCGGGTTGTCCTCGGCTGAAAATGCCCTACTAGTGGCTTTATTTGG
GTATGTGGGTTACCAGGCTCTCTCAAAGAGGCATGTCCCAATGATAACAGACATATATACCATCGAG
GACCAGAGACTAGAAGACACCACCCACCTCCAGTATGCACCCAACGCCATAAAAACCGATGGGACAG
AGACTGAACTGAAAGAACTGGCGTCGGGTGACGTGGAAAAAATCATGGGAGCCATTTCAGATTATGC
AGCTGGGGGACTGGAGTTTGTTAAATCCCAAGCAGAAAAGATAAAAACAGCTCCTTTGTTTAAAGAA
AACGCAGAAGCCGCAAAAGGGTATGTCCAAAAATTCATTGACTCATTAATTGAAAATAAAGAAGAAA
TAATCAGATATGGTTTGTGGGAACACACACAGCACTATACAAAAGCATAGCTGCAAGACTGGGGCA
TGAAACAGCGTTTGCCACACTAGTGTTAAAGTGGCTAGCTTTTGGAGGGGAATCAGTGTCAGACCAC
GTCAAGCAGGCGGCAGTTGATTTAGTGGTCTATTATGTGATGAATAAGCCTTCCTTCCCAGGTGACT
CCGAGACACAGCAAGAAGGGAGGCGATTCGTCGCAAGCCTGTTCATCTCCGCACTGGCAACCTACAC
ATACAAAACTTGGAATTACCACAATCTCTCTAAAGTGGTGGAACCAGCCCTGGCTTACCTCCCCTAT
GCTACCAGCGCATTAAAAA
TGTTCACCCCAACGCGGCTGGAGAGCGTGGTGATACTGAGCACCACGATATATAAAACATACCTCTC
TATAAGGAAGGGGAAGAGTGATGGATTGCTGGGTACGGGGATAAGTGCAGCCATGGAAATCCTGTCA
CAAAACCCAGTATCGGTAGGTATATCTGTGATGTTGGGGGTAGGGGCAATCGCTGCGCACAACGCTA
TTGAGTCCAGTGAACAGAAAAGGACCCTACTTATGAAGGTGTTTGTAAAGAACTTCTTGGATCAGGC
TGCAACAGATGAGCTGGTAAAAGAAAACCCAGAAAAAATTATAATGGCCTTATTTGAAGCAGTCCAG
ACAATTGGTAACCCCCTGAGACTAATATACCACCTGTATGGGGTTTACTACAAAGGTTGGGAGGCCA
AGGAACTATCTGAGAGGACAGCAGGCAGAAACTTATTCACATTGATAATGTTTGAAGCCTTCGAGTT
ATTAGGGATGGACTCACAAGGGAAAATAAGGAACCTGTCCGGAAATTACATTTTGGATTTGATATAC
GGCCTACACAAGCAAATCAACAGAGGGCTGAAGAAAATGGTACTGGGGTGGGCCCCTGCACCCTTTA
GTTGTGACTGGACCCCTAGTGACGAGAGGATCAGATTGCCAACAGACAACTATTTGAGGGTAGAAAC
CAGGTGCCCATGTGGCTATGAGATGAAAGCTTTCAAAAATGTAGGTGGCAAACTTACCAAAGTGGAG
GAGAGCGGGCCTTTCCTATGTAGAAACAGACCTGGTAGGGGACCAGTCAACTACAGAGTCACCAAGT
ATTACGATGACAACCTCAGAGAGATAAAACCAGTAGCAAAGTTGGAAGGACAGGTAGAGCACTACTA
CAAAGGGGTCACAGCAAAAATTGACTACAGTAAAGGAAAAATGCTCTTGGCCACTGACAAGTGGGAG
GTGGAACATGGTGTCATAACCAGGTTAGCTAAGAGATATACTGGGGTCGGGTTCAATGGTGCATACT
TAGGTGACGAGCCCAATCA
CCGTGCTCTAGTGGAGAGGGACTGTGCAACTATAACCAAAAACACAGTACAGTTTCTAAAAATGAAG
AAGGGGTGTGCGTTCACCTATGACCTGACCATCTCCAATCTGACCAGGCTCATCGAACTAGTACACA
GGAACAATCTTGAAGAGAAGGAAATACCCACCGCTACGGTCACCACATGGCTAGCTTACACCTTCGT
GAATGAAGACGTAGGGACTATAAAACCAGTACTAGGAGAGAGAGTAATCCCCGACCCTGTAGTTGAT
ATCAATTTACAACCAGAGGTGCAAGTGGACACGTCAGAGGTTGGGATCACAATAATTGGAAGGGAAA
CCCTGATGACAACGGGAGTGACACCTGTCTTGGAAAAAGTAGAGCCTGACGCCAGCGACAACCAAAA
CTCGGTGAAGATCGGGTTGGATGAGGGTAATTACCCAGGGCCTGGAATACAGACACATACACTAACA
GAAGAAATACACAACAGGGATGCGAGGCCCTTCATCATGATCCTGGGCTCAAGGAATTCCATATCAA
ATAGGGCAAAGACTGCTAGAAATATAAATCTGTACACAGGAAATGACCCCAGGGAAATACGAGACTT
```

Seq9pNADL890.txt

GATGGCTGCAGGGCGCATGTTAGTAGTAGCACTGAGGGATGTCGACCCTGAGCTGTCTGAAATGGTC
GATTTCAAGGGGACTTTTTAGATAGGGAGGCCCTGGAGGCTCTAAGTCTCGGGCAACCTAAACCGA
AGCAGGTTACCAAGGAAGCTGTTAGGAATTTGATAGAACAGAAAAAAGATGTGGAGATCCCTAACTG
GTTTGCATCAGATGACCCAGTATTTCTGGAAGTGGCCTTAAAAAATGATAAGTACTACTTAGTAGGA
GATGTTGGAGAGCTAAAAGATCAAGCTAAAGCACTTGGGGCCACGGATCAGACAAGAATTATAAAGG
AGGTAGGCTCAAGGACGTATGCCATGAAGCTATCTAGCTGGTTCCTCAAGGCATCAAACAAACAGAT
GAGTTTAACTCCACTGTTT
GAGGAATTGTTGCTACGGTGCCCACCTGCAACTAAGAGCAATAAGGGGCACATGGCATCAGCTTACC
AATTGGCACAGGGTAACTGGGAGCCCCTCGGTTGCGGGGTGCACCTAGGTACAATACCAGCCAGAAG
GGTGAAGATACACCCATATGAAGCTTACCTGAAGTTGAAAGATTTCATAGAAGAAGAAGAGAAGAAA
CCTAGGGTTAAGGATACAGTAATAAGAGAGCACAACAAATGGATACTTAAAAAAATAAGGTTTCAAG
GAAACCTCAACACCAAGAAAATGCTCAACCCAGGGAAACTATCTGAACAGTTGGACAGGGAGGGGCG
CAAGAGGAACATCTACAACCACCAGATTGGTACTATAATGTCAAGTGCAGGCATAAGGCTGGAGAAA
TTGCCAATAGTGAGGGCCCAAACCGACACCAAAACCTTTCATGAGGCAATAAGAGATAAGATAGACA
AGAGTGAAAACCGGCAAAATCCAGAATTGCACAACAAATTGTTGGAGATTTTCCACACGATAGCCCA
ACCCACCCTGAAACACACCTACGGTGAGGTGACGTGGGAGCAACTTGAGGCGGGGGTAAATAGAAAG
GGGGCAGCAGGCTTCCTGGAGAAGAAGAACATCGGAGAAGTATTGGATTCAGAAAAGCACCTGGTAG
AACAATTGGTCAGGGATCTGAAGGCCGGGAGAAAGATAAAATATTATGAAACTGCAATACCAAAAAA
TGAGAAGAGAGATGTCAGTGATGACTGGCAGGCAGGGGACCTGGTGGTTGAGAAGAGGCCAAGAGTT
ATCCAATACCCTGAAGCCAAGACAAGGCTAGCCATCACTAAGGTCATGTATAACTGGGTGAAACAGC
AGCCCGTTGTGATTCCAGGATATGAAGGAAAGACCCCCTTGTTCAACATCTTTGATAAAGTGAGAAA
GGAATGGGACTCGTTCAATGAGCCAGTGGCCGTAAGTTTTGACACCAAAGCCTGGGACACTCAAGTG
ACTAGTAAGGATCTGCAAC
TTATTGGAGAAATCCAGAAATATTACTATAAGAAGGAGTGGCACAAGTTCATTGACACCATCACCGA
CCACATGACAGAAGTACCAGTTATAACAGCAGATGGTGAAGTATATATAAGAAATGGGCAGAGAGGG
AGCGGCCAGCCAGACACAAGTGCTGGCAACAGCATGTTAAATGTCCTGACAATGATGTACGGCTTCT
GCGAAAGCACAGGGGTACCGTACAAGAGTTTCAACAGGGTGGCAAGGATCCACGTCTGTGGGGATGA
TGGCTTCTTAATAACTGAAAAAGGGTTAGGGCTGAAATTTGCTAACAAAGGGATGCAGATTCTTCAT
GAAGCAGGCAAACCTCAGAAGATAACGGAAGGGGAAAAGATGAAAGTTGCCTATAGATTTGAGGATA
TAGAGTTCTGTTCTCATACCCCAGTCCCTGTTAGGTGGTCCGACAACACCAGTAGTCACATGGCCGG
GAGAGACACCGCTGTGATACTATCAAAGATGGCAACAAGATTGGATTCAAGTGGAGAGAGGGGTACC
ACAGCATATGAAAAAGCGGTAGCCTTCAGTTTCTTGCTGATGTATTCCTGGAACCCGCTTGTTAGGA
GGATTTGCCTGTTGGTCCTTTCGCAACAGCCAGAGACAGACCCATCAAAACATGCCACTTATTATTA
CAAAGGTGATCCAATAGGGGCCTATAAAGATGTAATAGGTCGGAATCTAAGTGAACTGAAGAGAACA
GGCTTTGAGAAATTGGCAAATCTAAACCTAAGCCTGTCCACGTTGGGGGTCTGGACTAAGCACACAA
GCAAAAGAATAATTCAGGACTGTGTTGCCATTGGGAAAGAAGAGGGCAACTGGCTAGTTAAGCCCGA
CAGGCTGATATCCAGCAAAACTGGCCACTTATACATACCTGATAAAGGCTTTACATTACAAGGAAAG
CATTATGAGCAACTGCAGCTAAGAACAGAGACAAACCCGGTCATGGGGGTTGGGACTGAGAGATACA
AGTTAGGTCCCATAGTCAA
TCTGCTGCTGAGAAGGTTGAAAATTCTGCTCATGACGGCCGTCGGCGTCAGCAGCTGAGACAAAATG
TATATATTGTAAATAAATTAATCCATGTACATAGTGTATATAAATATAGTTGGACCGTCCACCTCA
AGAAGACGACACGCCCAACACGCACAGCTAAACAGTAGTCAAGATTATCTACCTCAAGATAACACTA
CATTTAATGCACACAGCACTTTAGCTGTATGAGGATACGCCCGACGTCTATAGTTGGACTAGGGAAG
ACCTCTAACAGCCCCCGCGGATCTAGAGGAGCATGCGACGTCAGGTGGCACTTTTCGGGGAAATGTG
CGCGGAACCCCTATTTGTTTATTTTTCTAAATACATTCAAATATGTATCCGCTCATGAGACAATAAC
CCTGATAAATGCTTCAATAATATTGAAAAAGGAAGAGTATGAGTATTCAACATTTCCGTGTCGCCCT
TATTCCCTTTTTTGCGGCATTTTGCCTTCCTGTTTTTGCTCACCCAGAAACGCTGGTGAAAGTAAAA
GATGCTGAAGATCAGTTGGGTGCACGAGTGGGTTACATCGAACTGGATCTCAACAGCGGTAAGATCC
TTGAGAGTTTTCGCCCCGAAGAACGTTTTCCAATGATGAGCACTTTTAAAGTTCTGCTATGTGGCGC
GGTATTATCCCGTATTGACGCCGGGCAAGAGCAACTCGGTCGCCGCATACACTATTCTCAGAATGAC
TTGGTTGAGTACTCACCAGTCACAGAAAAGCATCTTACGGATGGCATGACAGTAAGAGAATTATGCA
GTGCTGCCATAACCATGAGTGATAACACTGCGGCCAACTTACTTCTGACAACGATCGGAGGACCGAA

Seq9pNADL890.txt

GGAGCTAACCGCTTTTTTGCACAACATGGGGGATCATGTAACTCGCCTTGATCGTTGGGAACCGGAG
CTGAATGAAGCCATACCAAACGACGAGCGTGACACCACGATGCCTGTAGCAATGGCAACAACGTTGC
GCAAACTATTAACTGGCGA
ACTACTTACTCTAGCTTCCCGGCAACAATTAATAGACTGGATGGAGGCGGATAAAGTTGCAGGACCA
CTTCTGCGCTCGGCCCTTCCGGCTGGCTGGTTTATTGCTGATAAATCTGGAGCCGGTGAGCGTGGGT
CTCGCGGTATCATTGCAGCACTGGGGCCAGATGGTAAGCCCTCCCGTATCGTAGTTATCTACACGAC
GGGGAGTCAGGCAACTATGGATGAACGAAATAGACAGATCGCTGAGATAGGTGCCTCACTGATTAAG
CATTGGTAACTGTCAGACCAAGTTTACTCATATATACTTTAGATTGATTTAAAACTTCATTTTTAAT
TTAAAAGGATCTAGGTGAAGATCCTTTTTGATAATCTCATGACCAAAATCCCTTAACGTGAGTTTTC
GTTCCACTGAGCGTCAGACCCCGTAGAAAAGATCAAAGGATCTTCTTGAGATCCTTTTTTTCTGCGC
GTAATCTGCTGCTTGCAAACAAAAAAACCACCGCTACCAGCGGTGGTTTGTTTGCCGGATCAAGAGC
TACCAACTCTTTTTCCGAAGGTAACTGGCTTCAGCAGAGCGCAGATACCAAATACTGTCCTTCTAGT
GTAGCCGTAGTTAGGCCACCACTTCAAGAACTCTGTAGCACCGCCTACATACCTCGCTCTGCTAATC
CTGTTACCAGTGGCTGCTGCCAGTGGCGATAAGTCGTGTCTTACCGGGTTGGACTCAAGACGATAGT
TACCGGATAAGGCGCAGCGGTCGGGCTGAACGGGGGGTTCGTGCACACAGCCCAGCTTGGAGCGAAC
GACCTACACCGAACTGAGATACCTACAGCGTGAGCTATGAGAAAGCGCTCAAAGATGCAGGGGTAAA
AGCTAACCGCATCTTTACCGACAAGGCATCCGGCAGTTCAACAGATCGGGAAGGGCTGGATTTGCTG
AGGATGAAGGTGGAGGAAGGTGATGTCATTCTGGTGAAGAAGCTCGACCGTCTTGGCCGCGACACCG
CCGACATGATCCAACTGAT
AAAAGAGTTTGATGCTCAGGGTGTAGCGGTTCGGTTTATTGACGACGGGATCAGTACCGACGGTGAT
ATGGGGCAAATGGTGGTCACCATCCTGTCGGCTGTGGCACAGGCTGAACGCCGGAGGATCCTAGAGC
GCACGAATGAGGGCCGACAGGAAGCAAAGCTGAAAGGAATCAAATTTGGCCGCAGGCGTACCGTGGA
CAGGAACGTCGTGCTGACGCTTCATCAGAAGGGCACTGGTGCAACGGAAATTGCTCATCAGCTCAGT
ATTGCCCGCTCCACGGTTTATAAAATTCTTGAAGACGAAAGGGCCTCGTGATACGCCTATTTTTATA
GGTTAATGTCATGATAATAATGGTTTCTTAGACGTCAGGTGGCACTTTTCGGGGAAATGTGCGCGGA
ACCCCTATTTGTTTATTTTTCTAAATACATTCAAATATGTATCCGCTCATGAGACAATAACCCTGAT
AAATGCTTCAATAATATTGAAAAAGGAAGAGTATGAGTATTCAACATTTCCGTGTCGCCCTTATTCC
CTTTTTTGCGGCATTTTGCCTTCCTGTTTTTGCTCACCCAGAAACGCTGGTGAAAGTAAAAGATGCT
GAAGATCAGTTGGGTGCACGAGTGGGTTACATCGAACTGGATCTCAACAGCGGTAAGATCCTTGAGA
GTTTTCGCCCCGAAGAACGTTTTCCAATGATGAGCACTTTTAAAGTTCTGCTATGTGGCGCGGTATT
ATCCCGTGTTGACGCCGGGCAAGAGCAACTCGGTCGCCGCATACACTATTCTCAGAATGACTTGGTT
GAGTACTCACCAGTCACAGAAAAGCATCTTACGGATGGCATGACAGTAAGAGAATTATGCAGTGCTG
CCATAACCATGAGTGATAACACTGCGGCCAACTTACTTCTGACAACGATCGGAGGACCGAAGGAGCT
AACCGCTTTTTTGCACAACATGGGGGATCATGTAACTCGCCTTGATCGTTGGGAACCGGAGCTGAAT
GAAGCCATACCAAACGACG
AGCGTGACACCACGATGCCTGCAGCAATGGCAACAACGTTGCGCAAACTATTAACTGGCGAACTACT
TACTCTAGCTTCCCGGCAACAATTAATAGACTGGATGGAGGCGGATAAAGTTGCAGGACCACTTCTG
CGCTCGGCCCTTCCGGCTGGCTGGTTTATTGCTGATAAATCTGGAGCCGGTGAGCGTGGGTCTCGCG
GTATCATTGCAGCACTGGGGCCAGATGGTAAGCCCTCCCGTATCGTAGTTATCTACACGACGGGGAG
TCAGGCAACTATGGATGAACGAAATAGACAGATCGCTGAGATAGGTGCCTCACTGATTAAGCATTGG
TAACTGTCAGACCAAGTTTACTCATATATACTTTAGATTGATTTAAAACTTCATTTTTAATTTAAAA
GGATCTAGGTGAAGATCCTTTTTGATAATCTCATGACCAAAATCCCTTAACGTGAGTTTTCGTTCCA
CTGAGCGTCAGACCCCTTAATAAGATGATCTTCTTGAGATCGTTTTGGTCTGCGCGTAATCTCTTGC
TCTGAAAACGAAAAAACCGCCTTGCAGGGCGGTTTTTCGAAGGTTCTCTGAGCTACCAACTCTTTGA
ACCGAGGTAACTGGCTTGGAGGAGCGCAGTCACCAAAACTTGTCCTTTCAGTTTAGCCTTAACCGGC
GCATGACTTCAAGACTAACTCCTCTAAATCAATTACCAGTGGCTGCTGCCAGTGGTGCTTTTGCATG
TCTTTCCGGGTTGGACTCAAGACGATAGTTACCGGATAAGGCGCAGCGGTCGGACTGAACGGGGGGT
TCGTGCATACAGTCCAGCTTGGAGCGAACTGCCTACCCGGAACTGAGTGTCAGGCGTGGAATGAGAC
AAACGCGGCCATAACAGCGGAATGACACCGGTAAACCGAAAGGCAGGAACAGGAGAGCGCACGAGGG
AGCCGCCAGGGGGAAACGCCTGGTATCTTTATAGTCCTGTCGGGTTTCGCCACCACTGATTTGAGCG
TCAGATTTCGTGATGCTTG
TCAGGGGGGCGGAGCCTATGGAAAAACGGCTTTGCCGCGGCCCTCTCACTTCCCTGTTAAGTATCTT

Seq9pNADL890.txt

```
CCTGGCATCTTCCAGGAAATCTCCGCCCCGTTCGTAAGCCATTTCCGCTCGCCGCAGTCGAACGACC
GAGCGTAGCGAGTCAGTGAGCGAGGAAGCGGAATATATCCTGTATCACATATTCTGCTGACGCACCG
GTGCAGCCTTTTTTCTCCTGCCACATGAAGCACTTCACTGACACCCTCATCAGTGCCAACATAGTAA
GCCAGTATACACTCCGCTAGCGCCACGCGTATCGATGAATTCGTTAATACGACTCACTATA
```

Phenotype analysis of hybrid virus vs NADL and 890 at 24hr post infection

NADL890

NADL

SEQUENCE LISTING

<160> NUMBER OF SEQ ID NOS: 12

<210> SEQ ID NO 1
<211> LENGTH: 34
<212> TYPE: DNA
<213> ORGANISM: Artificial Sequence
<220> FEATURE:
<223> OTHER INFORMATION: Oligonucleotide 890E1a 5'-forward primer

<400> SEQUENCE: 1
ccatactgcg atgtggatcg gaagatcggt tacg 34

<210> SEQ ID NO 2
<211> LENGTH: 39
<212> TYPE: DNA
<213> ORGANISM: Artificial Sequence
<220> FEATURE:
<223> OTHER INFORMATION: Oligonucleotide 890NADLE2a 3'-reverse primer

<400> SEQUENCE: 2
ccaaagtaca tatctgccac ccaacaaggc gaccactgc 39

<210> SEQ ID NO 3
<211> LENGTH: 36
<212> TYPE: DNA
<213> ORGANISM: Artificial Sequence
<220> FEATURE:
<223> OTHER INFORMATION: Oligonucleotide NADL890E2a 5'-forward primer

<400> SEQUENCE: 3
gtggtcgcct tgttgggtgg cagatatgta ctttgg 36

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide NADLNS2a 3'-reverse primer

<400> SEQUENCE: 4
cagccacgtc aaccttccac ctcg 24

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide NADLC5 5'-forward primer

<400> SEQUENCE: 5
cagaaacccg acagactaga aagg 24

<210> SEQ ID NO 6
<211> LENGTH: 25
<212> TYPE: DNA
<213> ORGANISM: Artificial Sequence
<220> FEATURE:
<223> OTHER INFORMATION: Oligonucleotide NADLp7 3'-reverse primer

<400> SEQUENCE: 6
gtacagcagc aagaagtatg tcacc 25

<210> SEQ ID NO 7
<211> LENGTH: 20
<212> TYPE: DNA
<213> ORGANISM: Artificial Sequence
<220> FEATURE:
<223> OTHER INFORMATION: Olingonucleotide Seq2(+)5'-forward primer

<400> SEQUENCE: 7
ggagcatacg ctgcttcccc 20

<210> SEQ ID NO 8
<211> LENGTH: 19
<212> TYPE: DNA
<213> ORGANISM: Artificial Sequence
<220> FEATURE:
<223> OTHER INFORMATION: Oligonucleotide NADLE06(+) 5'-forward primer

<400> SEQUENCE: 8
cgccatgagt ggaacaagc 19

<210> SEQ ID NO 9
<211> LENGTH: 16713
<212> TYPE: DNA
<213> ORGANISM: Artificial Sequence
<220> FEATURE:
<223> OTHER INFORMATION: pNADL890 vector

<400> SEQUENCE: 9
gtatacgaga attagaaaag gcactcgtat acgtattggg caattaaaaa taataattag 60
gcctagggaa caaatccctc tcagcgaagg ccgaaaagag gctagccatg cccttagtag 120
gactagcata atgagggggg tagcaacagt ggtgagttcg ttggatggct taagccctga 180
gtacagggta gtcgtcagtg gttcgacgcc ttggaataaa ggtctcgaga tgccacgtgg 240
acgagggcat gcccaaagca catcttaacc tgagcggggg tcgcccaggt aaaagcagtt 300
ttaaccgact gttacgaata cagcctgata gggtgctgca gaggcccact gtattgctac 360
taaaaatctc tgctgtacat ggcacatgga gttgatcaca aatgaacttt tatacaaaac 420
atacaaacaa aaacccgtcg ggtggaggaa acctgtttat gatcaggcag gtgatccctt 480
atttggtgaa aggggagcag tccaccctca atcgacgcta aagctcccac acaagagagg 540
ggaacgcgat gttccaacca acttggcatc cttaccaaaa agaggtgact gcaggtcggg 600
taatagcaga ggacctgtga gcgggatcta cctgaagcca gggccactat tttaccagga 660
ctataaaggt cccgtctatc acagggcccc gctggagctc tttgaggagg gatccatgtg 720
tgaaacgact aaacggatag ggagagtaac tggaagtgac ggaaagctgt accacattta 780
tgtgtgtata gatggatgta taataataaa aagtgccacg agaagttacc aaagggtgtt 840
caggtgggtc cataataggc ttgactgccc tctatgggtc acaagttgct cagacacgaa 900
agaagaggga gcaacaaaaa agaaaacaca gaaacccgac agactagaaa gggggaaaat 960
gaaaatagtg cccaaagaat ctgaaaaaga cagcaaaact aaacctccgg atgctacaat 1020
agtggtggaa ggagtcaaat accaggtgag gaagaaggga aaaaccaaga gtaaaaacac 1080
tcaggacggc ttgtaccata acaaaaacaa acctcaggaa tcacgcaaga aactggaaaa 1140
agcattgttg gcgtgggcaa taatagctat agttttgttt caagttacaa tgggagaaaa 1200
cataacacag tggaacctac aagataatgg gacggaaggg atacaacggg caatgttcca 1260

-continued

```
aaggggtgtg aatagaagtt tacatggaat ctggccagag aaaatctgta ctggcgtccc   1320
ttcccatcta gccaccgata tagaactaaa aacaattcat ggtatgatgg atgcaagtga   1380
gaagaccaac tacacgtgtt gcagacttca acgccatgag tggaacaagc atggttggtg   1440
caactggtac aatattgaac cctggattct agtcatgaat agaacccaag ccaatctcac   1500
tgagggacaa ccaccaaggg agtgcgcagt cacttgtagg tatgataggg ctagtgactt   1560
aaacgtggta acacaagcta gagatagccc cacaccctta acaggttgca agaaaggaaa   1620
gaacttctcc tttgcaggca tattgatgcg gggcccctgc aactttgaaa tagctgcaag   1680
tgatgtatta ttcaaagaac atgaacgcat tagtatgttc caggatacta ctctttacct   1740
tgttgacggg ttgaccaact ccttagaagg tgccagacaa ggaaccgcta aactgacaac   1800
ctggttaggc aagcagctcg ggatactagg aaaaaagttg gaaaacaaga gtaagacgtg   1860
gtttggagca tacgctgctt ccccttactg tgatgtggat cggaagatcg gttacgtctg   1920
gtatacaaaa aactgcactc cagcttgcct cccaagaaac accaagataa taggccccgg   1980
gaagtttgac accaacgccg aagatggcaa aatactccat gagatgggag ggcacctctc   2040
agaatttgcc ctattgtcct tggtggttct gtctgacttt gccccagaaa ccgcgagtgt   2100
catctacttg gttctacatt ttgcgatccc gcaaagccac gttgatgtag acacatgcga   2160
caagaaccag ctgaatttaa cggtcgcaac tacagtagca gaagtcatac cagggacagt   2220
gtggaaccta gggaagtatg tctgcataag accggactgg tggccatatg agacgacgac   2280
agtcttcgtc ttagaggaag cagggcaagt aatcaaattg ggcctaaggg ccatcagaga   2340
cttaactagg atatggaacg ctgccaccac cacagctttc ctaatctttt tagtgaaagc   2400
actgagggga caactaatcc aagggctatt gtggctgatg ctaataacag gagctcaggg   2460
cttccctgaa tgcaaggagg gcttccaata tgccatatcg aaagacagaa aaatggggtt   2520
attggggcca gagagcttaa ctacaacatg gcaccgtccc acaaaaaaat tagtggactc   2580
catggtacaa gtatggtgtg aaggaaaaga cttgaaaata ttaaaaacgt gccccaagga   2640
agagaggtac ctagtggctg tgcacgagag agccctatca accagtgctg agtttatgcc   2700
aatcagtgat gggacaatag gcccagatgt gatagatatg cctgatgact ttgagtttgg   2760
actctgccct tgtgacgcaa aaccagtgat aaagggcaaa tttaatgcca gcttactgaa   2820
tggaccagct ttccagatgg tatgcccaca ggggtggact ggtacaatag aatgcaccct   2880
ggcgaaccaa gacaccttag acacaactgt ggttaggaca tacagaagaa ctactccatt   2940
tcagcggaga aaatggtgct cctatgaaaa aataataggg gaagatatcc atgaatgcat   3000
tctgggtgga actggacat gcataactgg tgaccatagc aagttgaaag acggacctat   3060
caagaaatgt aagtggtgtg gctatgactt cgtcaactca gagggactgc cacactaccc   3120
aataggtaag tgcatgctca tcaatgagag tgggtacagg tatgtagatg acacctcttg   3180
cgataggggt ggtgtagcca tagtcccaac aggcaccgta aagtgtagaa taggtgacgt   3240
cacggtgcag gttgtcgctt ctaataatga tctgggaccc atgccctgca gcccagctga   3300
agtgatagca agtgaaggac cagtggaaaa gactgcatgc acatttaact attcaaggac   3360
actacccaat aagtattatg agccaaggga ccgttacttc caacaataca tgctaaaagg   3420
ggagtggcaa tattggtttg acctggatca tgtagaccac cacaaagact acttctcaga   3480
gttcataatc atagcagtgg tcgccttgtt gggtggcaga tatgtacttt ggttactggt   3540
tacatacatg gtcttatcag aacagaaggc cttagggatt cagtatggat caggggaagt   3600
```

-continued

```
ggtgatgatg ggcaacttgc taacccataa caatattgaa gtggtgacat acttcttgct   3660
gctgtaccta ctgctgaggg aggagagcgt aaagaagtgg gtcttactct tataccacat   3720
cttagtggta cacccaatca aatctgtaat tgtgatccta ctgatgattg ggatgtggt    3780
aaaggccgat tcaggggggcc aagagtactt ggggaaaata gacctctgtt ttacaacagt   3840
agtactaatc gtcataggtt taatcatagc caggcgtgac ccaactatag tgccactggt   3900
aacaataatg gcagcactga gggtcactga actgacccac cagcctggag ttgacatcgc   3960
tgtggcggtc atgactataa ccctactgat ggttagctat gtgacagatt attttagata   4020
taaaaaatgg ttacagtgca ttctcagcct ggtatctggg gtgttcttga taagaagcct   4080
aatataccta ggtagaatcg agatgccaga ggtaactatc ccaaactgga gaccactaac   4140
tttaatacta ttatatttga tctcaacaac aattgtaacg aggtggaagg ttgacgtggc   4200
tggcctattg ttgcaatgtg tgcctatctt attgctggtc acaaccttgt gggccgactt   4260
cttaacccta atactgatcc tgcctaccta tgaattggtt aaattatact atctgaaaac   4320
tgttaggact gatatagaaa gaagttggct agggggggata gactatacaa gagttgactc   4380
catctacgac gttgatgaga gtggagaggg cgtatatctt tttccatcaa ggcagaaagc   4440
acaggggaat ttttctatac tcttgcccct tatcaaagca acactgataa gttgcgtcag   4500
cagtaaatgg cagctaatat acatgagtta cttaactttg gactttatgt actacatgca   4560
caggaaagtt atagaagaga tctcaggagg taccaacata atatccaggt tagtggcagc   4620
actcatagag ctgaactggt ccatggaaga agaggagagc aaaggcttaa agaagtttta   4680
tctattgtct ggaaggttga gaaacctaat aataaaacat aaggtaagga atgagaccgt   4740
ggcttcttgg tacggggagg aggaagtcta cggtatgcca aagatcatga ctataatcaa   4800
ggccagtaca ctgagtaaga gcaggcactg cataatatgc actgtatgtg agggccgaga   4860
gtggaaaggt ggcacctgcc caaaatgtgg acgccatggg aagccgataa cgtgtgggat   4920
gtcgctagca gatttcgaag aaagacacta taaaagaatc tttataaggg aaggcaactt   4980
tgagggtatg tgcagccgat gccagggaaa gcataggagg tttgaaatgg accgggaacc   5040
taagagtgcc agatactgtg ctgagtgtaa taggctgcat cctgctgagg aaggtgactt   5100
ttgggcagag tcgagcatgt tgggcctcaa aatcacctac tttgcgctga tggatggaaa   5160
ggtgtatgat atcacagagt gggctggatg ccagcgtgtg ggaatctccc cagataccca   5220
cagagtccct tgtcacatct catttggttc acggatgcct ttcaggcagg aatacaatgg   5280
ctttgtacaa tataccgcta gggggcaact atttctgaga aacttgcccg tactggcaac   5340
taaagtaaaa atgctcatgg taggcaacct tggagaagaa attggtaatc tggaacatct   5400
tgggtggatc ctaagggggc ctgccgtgtg taagaagatc acagagcacg aaaaatgcca   5460
cattaatata ctggataaac taaccgcatt tttcgggatc atgccaaggg ggactacacc   5520
cagagccccg gtgaggttcc ctacgagctt actaaaagtg aggaggggtc tggagactgg   5580
ctgggcttac acacaccaag gcgggataag ttcagtcgac catgtaaccg ccggaaaaga   5640
tctactggtc tgtgacagca tgggacgaac tagagtggtt tgccaaagca acaacaggtt   5700
gaccgatgag acagagtatg gcgtcaagac tgactcaggg tgcccagacg gtgccagatg   5760
ttatgtgtta aatccagagg ccgttaacat atcaggatcc aaaggggcag tcgttcacct   5820
ccaaaagaca ggtggagaat tcacgtgtgt caccgcatca ggcacaccgg ctttcttcga   5880
cctaaaaaac ttgaaaggat ggtcaggctt gcctatattt gaagcctcca gcgggagggt   5940
ggttggcaga gtcaaagtag ggaagaatga agagtctaaa cctacaaaaa taatgagtgg   6000
```

-continued

```
aatccagacc gtctcaaaaa acacagcaga cctgaccgag atggtcaaga agataaccag   6060
catgaacagg ggagacttca agcagattac tttggcaaca ggggcaggca aaaccacaga   6120
actcccaaaa gcagttatag aggagatagg aagacacaag agagtattag ttcttatacc   6180
attaagggca gcggcagagt cagtctacca gtatatgaga ttgaaacacc caagcatctc   6240
ttttaaccta aggatagggg acatgaaaga gggggacatg gcaaccggga taacctatgc   6300
atcatacggg tacttctgcc aaatgcctca accaaagctc agagctgcta tggtagaata   6360
ctcatacata ttcttagatg aataccattg tgccactcct gaacaactgg caattatcgg   6420
gaagatccac agattttcag agagtataag ggttgtcgcc atgactgcca cgccagcagg   6480
gtcggtgacc acaacaggtc aaaagcaccc aatagaggaa ttcatagccc ccgaggtaat   6540
gaaaggggag gatcttggta gtcagttcct tgatatagca gggttaaaaa taccagtgga   6600
tgagatgaaa ggcaatatgt tggtttttgt accaacgaga aacatggcag tagaggtagc   6660
aaagaagcta aaagctaagg gctataactc tggatactat tacagtggag aggatccagc   6720
caatctgaga gttgtgacat cacaatcccc ctatgtaatc gtggctacaa atgctattga   6780
atcaggagtg acactaccag atttggacac ggttatagac acggggttga aatgtgaaaa   6840
gagggtgagg gtatcatcaa agataccctt catcgtaaca ggccttaaga ggatggccgt   6900
gactgtgggt gagcaggcgc agcgtagggg cagagtaggt agagtgaaac ccgggaggta   6960
ttataggagc caggaaacag caacagggtc aaaggactac cactatgacc tcttgcaggc   7020
acaaagatac gggattgagg atggaatcaa cgtgacgaaa tcctttaggg agatgaatta   7080
cgattggagc ctatacgagg aggacagcct actaataacc cagctggaaa tactaaataa   7140
tctactcatc tcagaagact tgccagccgc tgttaagaac ataatggcca ggactgatca   7200
cccagagcca atccaacttg catacaacag ctatgaagtc caggtcccgg tcctattccc   7260
aaaaataagg aatggagaag tcacagacac ctacgaaaat tactcgtttc taaatgccag   7320
aaagttaggg gaggatgtgc ccgtgtatat ctacgctact gaagatgagg atctggcagt   7380
tgacctctta gggctagact ggcctgatcc tgggaaccag caggtagtgg agactggtaa   7440
agcactgaag caagtgaccg ggttgtcctc ggctgaaaat gccctactag tggctttatt   7500
tgggtatgtg ggttaccagg ctctctcaaa gaggcatgtc ccaatgataa cagacatata   7560
taccatcgag gaccagagac tagaagacac cacccacctc cagtatgcac ccaacgccat   7620
aaaaaccgat gggacagaga ctgaactgaa agaactggcg tcgggtgacg tggaaaaaat   7680
catgggagcc atttcagatt atgcagctgg gggactggag tttgttaaat cccaagcaga   7740
aaagataaaa acagctcctt tgtttaaaga aaacgcagaa gccgcaaaag ggtatgtcca   7800
aaaattcatt gactcattaa ttgaaaataa agaagaaata atcagatatg gtttgtgggg   7860
aacacacaca gcactataca aaagcatagc tgcaagactg gggcatgaaa cagcgtttgc   7920
cacactagtg ttaaagtggc tagcttttgg aggggaatca gtgtcagacc acgtcaagca   7980
ggcggcagtt gatttagtgg tctattatgt gatgaataag ccttccttcc caggtgactc   8040
cgagacacag caagaaggga ggcgattcgt cgcaagcctg ttcatctccg cactggcaac   8100
ctacacatac aaaacttgga attaccacaa tctctctaaa gtggtggaac cagccctggc   8160
ttacctcccc tatgctacca gcgcattaaa aatgttcacc ccaacgcggc tggagagcgt   8220
ggtgatactg agcaccacga tatataaaac atacctctct ataaggaagg ggaagagtga   8280
tggattgctg ggtacgggga taagtgcagc catggaaatc ctgtcacaaa acccagtatc   8340
```

-continued

```
ggtaggtata tctgtgatgt tgggggtagg ggcaatcgct gcgcacaacg ctattgagtc   8400
cagtgaacag aaaaggaccc tacttatgaa ggtgtttgta aagaacttct tggatcaggc   8460
tgcaacagat gagctggtaa aagaaaaccc agaaaaaatt ataatggcct tatttgaagc   8520
agtccagaca attggtaacc ccctgagact aatataccac ctgtatgggg tttactacaa   8580
aggttgggag gccaaggaac tatctgagag gacagcaggc agaaacttat tcacattgat   8640
aatgtttgaa gccttcgagt tattagggat ggactcacaa gggaaaataa ggaacctgtc   8700
cggaaattac attttggatt tgatatacgg cctacacaag caaatcaaca gagggctgaa   8760
gaaaatggta ctggggtggg cccctgcacc ctttagttgt gactggaccc ctagtgacga   8820
gaggatcaga ttgccaacag acaactattt gagggtagaa accaggtgcc catgtggcta   8880
tgagatgaaa gctttcaaaa atgtaggtgg caaacttacc aaagtggagg agagcgggcc   8940
tttcctatgt agaaacagac ctggtagggg accagtcaac tacagagtca ccaagtatta   9000
cgatgacaac ctcagagaga taaaaccagt agcaaagttg gaaggacagg tagagcacta   9060
ctacaaaggg gtcacagcaa aaattgacta cagtaaagga aaaatgctct tggccactga   9120
caagtgggag gtggaacatg gtgtcataac caggttagct aagagatata ctggggtcgg   9180
gttcaatggt gcatacttag gtgacgagcc caatcaccgt gctctagtgg agagggactg   9240
tgcaactata accaaaaaca cagtacagtt tctaaaaatg aagaaggggt gtgcgttcac   9300
ctatgacctg accatctcca atctgaccag gctcatcgaa ctagtacaca ggaacaatct   9360
tgaagagaag gaaataccca ccgctacggt caccacatgg ctagcttaca ccttcgtgaa   9420
tgaagacgta gggactataa aaccagtact aggagagaga gtaatccccg accctgtagt   9480
tgatatcaat ttacaaccag aggtgcaagt ggacacgtca gaggttggga tcacaataat   9540
tggaagggaa accctgatga caacgggagt gacacctgtc ttggaaaaag tagagcctga   9600
cgccagcgac aaccaaaact cggtgaagat cgggttggat gagggtaatt acccagggcc   9660
tggaatacag acacatacac taacagaaga aatacacaac agggatgcga ggcccttcat   9720
catgatcctg ggctcaagga attccatatc aaatagggca aagactgcta gaaatataaa   9780
tctgtacaca ggaaatgacc ccagggaaat acgagacttg atggctgcag ggcgcatgtt   9840
agtagtagca ctgagggatg tcgaccctga gctgtctgaa atggtcgatt tcaaggggac   9900
ttttttagat agggaggccc tggaggctct aagtctcggg caacctaaac cgaagcaggt   9960
taccaaggaa gctgttagga atttgataga acagaaaaaa gatgtggaga tccctaactg  10020
gtttgcatca gatgacccag tatttctgga agtggcctta aaaaatgata agtactactt  10080
agtaggagat gttggagagc taaaagatca agctaaagca cttggggcca cggatcagac  10140
aagaattata aaggaggtag gctcaaggac gtatgccatg aagctatcta gctggttcct  10200
caaggcatca aacaaacaga tgagtttaac tccactgttt gaggaattgt tgctacggtg  10260
cccacctgca actaagagca ataaggggca catggcatca gcttaccaat tggcacaggg  10320
taactgggag cccctcggtt gcggggtgca cctaggtaca ataccagcca gaagggtgaa  10380
gatacaccca tatgaagctt acctgaagtt gaaagatttc atagaagaag aagagaagaa  10440
acctagggtt aaggatacag taataagaga gcacaacaaa tggatactta aaaaaataag  10500
gtttcaagga aacctcaaca ccaagaaaat gctcaaccca gggaaactat ctgaacagtt  10560
ggacagggag gggcgcaaga ggaacatcta caaccaccag attggtacta taatgtcaag  10620
tgcaggcata aggctggaga aattgccaat agtgagggcc caaaccgaca ccaaaacctt  10680
tcatgaggca ataagagata agatagacaa gagtgaaaac cggcaaaatc cagaattgca  10740
```

-continued

```
caacaaattg ttggagattt tccacacgat agcccaaccc accctgaaac acacctacgg  10800
tgaggtgacg tgggagcaac ttgaggcggg ggtaaataga aagggggcag caggcttcct  10860
ggagaagaag aacatcggag aagtattgga ttcagaaaag cacctggtag aacaattggt  10920
cagggatctg aaggccggga gaaagataaa atattatgaa actgcaatac caaaaaatga  10980
gaagagagat gtcagtgatg actggcaggc aggggacctg gtggttgaga agaggccaag  11040
agttatccaa taccctgaag ccaagacaag gctagccatc actaaggtca tgtataactg  11100
ggtgaaacag cagcccgttg tgattccagg atatgaagga aagacccccct tgttcaacat  11160
ctttgataaa gtgagaaagg aatgggactc gttcaatgag ccagtggccg taagttttga  11220
caccaaagcc tgggacactc aagtgactag taaggatctg caacttattg gagaaatcca  11280
gaaatattac tataagaagg agtggcacaa gttcattgac accatcaccg accacatgac  11340
agaagtacca gttataacag cagatggtga agtatatata agaaatgggc agagagggag  11400
cggccagcca gacacaagtg ctggcaacag catgttaaat gtcctgacaa tgatgtacgg  11460
cttctgcgaa agcacagggg taccgtacaa gagtttcaac agggtggcaa ggatccacgt  11520
ctgtggggat gatggcttct taataactga aaaagggtta gggctgaaat ttgctaacaa  11580
agggatgcag attcttcatg aagcaggcaa acctcagaag ataacggaag ggaaaaagat  11640
gaaagttgcc tatagatttg aggatataga gttctgttct catacccccag tccctgttag  11700
gtggtccgac aacaccagta gtcacatggc cgggagagac accgctgtga tactatcaaa  11760
gatggcaaca agattggatt caagtggaga gaggggtacc acagcatatg aaaaagcggt  11820
agccttcagt ttcttgctga tgtattcctg gaacccgctt gttaggagga tttgcctgtt  11880
ggtcctttcg caacagccag agacagaccc atcaaaacat gccacttatt attacaaagg  11940
tgatccaata ggggcctata aagatgtaat aggtcggaat ctaagtgaac tgaagagaac  12000
aggctttgag aaattggcaa atctaaacct aagcctgtcc acgttggggg tctggactaa  12060
gcacacaagc aaaagaataa ttcaggactg tgttgccatt gggaaagaag agggcaactg  12120
gctagttaag cccgacaggc tgatatccag caaaactggc cacttataca tacctgataa  12180
aggctttaca ttacaaggaa agcattatga gcaactgcag ctaagaacag agacaaaccc  12240
ggtcatgggg gttgggactg agagatacaa gttaggtccc atagtcaatc tgctgctgag  12300
aaggttgaaa attctgctca tgacggccgt cggcgtcagc agctgagaca aaatgtatat  12360
attgtaaata aattaatcca tgtacatagt gtatataaat atagttggga ccgtccacct  12420
caagaagacg acacgcccaa cacgcacagc taaacagtag tcaagattat ctacctcaag  12480
ataacactac atttaatgca cacagcactt tagctgtatg aggatacgcc cgacgtctat  12540
agttggacta gggaagacct ctaacagccc ccgcggatct agaggagcat gcgacgtcag  12600
gtggcacttt tcggggaaat gtgcgcggaa cccctatttg tttatttttc taaatacatt  12660
caaatatgta tccgctcatg agacaataac cctgataaat gcttcaataa tattgaaaaa  12720
ggaagagtat gagtattcaa catttccgtg tcgcccttat tccctttttt gcggcatttt  12780
gccttcctgt ttttgctcac ccagaaacgc tggtgaaagt aaaagatgct gaagatcagt  12840
tgggtgcacg agtgggttac atcgaactgg atctcaacag cggtaagatc cttgagagtt  12900
ttcgccccga agaacgtttt ccaatgatga gcacttttaa agttctgcta tgtggcgcgg  12960
tattatcccg tattgacgcc gggcaagagc aactcggtcg ccgcatacac tattctcaga  13020
atgacttggt tgagtactca ccagtcacag aaaagcatct tacggatggc atgacagtaa  13080
```

-continued

```
gagaattatg cagtgctgcc ataaccatga gtgataacac tgcggccaac ttacttctga  13140
caacgatcgg aggaccgaag gagctaaccg cttttttgca caacatgggg gatcatgtaa  13200
ctcgccttga tcgttgggaa ccggagctga atgaagccat accaaacgac gagcgtgaca  13260
ccacgatgcc tgtagcaatg gcaacaacgt tgcgcaaact attaactggc gaactactta  13320
ctctagcttc ccggcaacaa ttaatagact ggatggaggc ggataaagtt gcaggaccac  13380
ttctgcgctc ggcccttccg gctggctggt ttattgctga taaatctgga gccggtgagc  13440
gtgggtctcg cggtatcatt gcagcactgg ggccagatgg taagccctcc cgtatcgtag  13500
ttatctacac gacggggagt caggcaacta tggatgaacg aaatagacag atcgctgaga  13560
taggtgcctc actgattaag cattggtaac tgtcagacca agtttactca tatatacttt  13620
agattgattt aaaacttcat ttttaattta aaaggatcta ggtgaagatc ctttttgata  13680
atctcatgac caaaatccct taacgtgagt tttcgttcca ctgagcgtca gaccccgtag  13740
aaaagatcaa aggatcttct tgagatcctt tttttctgcg cgtaatctgc tgcttgcaaa  13800
caaaaaaacc accgctacca gcggtggttt gtttgccgga tcaagagcta ccaactcttt  13860
ttccgaaggt aactggcttc agcagagcgc agataccaaa tactgtcctt ctagtgtagc  13920
cgtagttagg ccaccacttc aagaactctg tagcaccgcc tacatacctc gctctgctaa  13980
tcctgttacc agtggctgct gccagtggcg ataagtcgtg tcttaccggg ttggactcaa  14040
gacgatagtt accggataag gcgcagcggt cgggctgaac ggggggttcg tgcacacagc  14100
ccagcttgga gcgaacgacc tacaccgaac tgagatacct acagcgtgag ctatgagaaa  14160
gcgctcaaag atgcaggggt aaaagctaac cgcatcttta ccgacaaggc atccggcagt  14220
tcaacagatc gggaagggct ggatttgctg aggatgaagg tggaggaagg tgatgtcatt  14280
ctggtgaaga agctcgaccg tcttggccgc gacaccgccg acatgatcca actgataaaa  14340
gagtttgatg ctcagggtgt agcggttcgg tttattgacg acgggatcag taccgacggt  14400
gatatggggc aaatggtggt caccatcctg tcggctgtgg cacaggctga acgccggagg  14460
atcctagagc gcacgaatga gggccgacag gaagcaaagc tgaaaggaat caaatttggc  14520
cgcaggcgta ccgtggacag gaacgtcgtg ctgacgcttc atcagaaggg cactggtgca  14580
acggaaattg ctcatcagct cagtattgcc cgctccacgg tttataaaat tcttgaagac  14640
gaaagggcct cgtgatacgc ctatttttat aggttaatgt catgataata atggtttctt  14700
agacgtcagg tggcactttt cggggaaatg tgcgcggaac ccctatttgt ttatttttct  14760
aaatacattc aaatatgtat ccgctcatga gacaataacc ctgataaatg cttcaataat  14820
attgaaaaag gaagagtatg agtattcaac atttccgtgt cgcccttatt cccttttttg  14880
cggcattttg ccttcctgtt tttgctcacc cagaaacgct ggtgaaagta aaagatgctg  14940
aagatcagtt gggtgcacga gtgggttaca tcgaactgga tctcaacagc ggtaagatcc  15000
ttgagagttt tcgccccgaa gaacgttttc caatgatgag cacttttaaa gttctgctat  15060
gtggcgcggt attatcccgt gttgacgccg ggcaagagca actcggtcgc cgcatacact  15120
attctcagaa tgacttggtt gagtactcac cagtcacaga aaagcatctt acggatggca  15180
tgacagtaag agaattatgc agtgctgcca taaccatgag tgataacact gcggccaact  15240
tacttctgac aacgatcgga ggaccgaagg agctaaccgc ttttttgcac aacatggggg  15300
atcatgtaac tcgccttgat cgttgggaac cggagctgaa tgaagccata ccaaacgacg  15360
agcgtgacac cacgatgcct gcagcaatgg caacaacgtt gcgcaaacta ttaactggcg  15420
aactacttac tctagcttcc cggcaacaat taatagactg gatggaggcg gataaagttg  15480
```

```
caggaccact tctgcgctcg gcccttccgg ctggctggtt tattgctgat aaatctggag  15540
ccggtgagcg tgggtctcgc ggtatcattg cagcactggg gccagatggt aagccctccc  15600
gtatcgtagt tatctacacg acggggagtc aggcaactat ggatgaacga aatagacaga  15660
tcgctgagat aggtgcctca ctgattaagc attggtaact gtcagaccaa gtttactcat  15720
atatacttta gattgattta aaacttcatt tttaatttaa aaggatctag gtgaagatcc  15780
tttttgataa tctcatgacc aaaatccctt aacgtgagtt ttcgttccac tgagcgtcag  15840
accccttaat aagatgatct tcttgagatc gttttggtct gcgcgtaatc tcttgctctg  15900
aaaacgaaaa aaccgccttg cagggcggtt tttcgaaggt tctctgagct accaactctt  15960
tgaaccgagg taactggctt ggaggagcgc agtcaccaaa acttgtcctt tcagtttagc  16020
cttaaccggc gcatgacttc aagactaact cctctaaatc aattaccagt ggctgctgcc  16080
agtggtgctt ttgcatgtct ttccgggttg gactcaagac gatagttacc ggataaggcg  16140
cagcggtcgg actgaacggg gggttcgtgc atacagtcca gcttggagcg aactgcctac  16200
ccggaactga gtgtcaggcg tggaatgaga caaacgcggc cataacagcg gaatgacacc  16260
ggtaaaccga aggcaggaa caggagagcg cacgagggag ccgccagggg gaaacgcctg  16320
gtatctttat agtcctgtcg ggtttcgcca ccactgattt gagcgtcaga tttcgtgatg  16380
cttgtcaggg gggcggagcc tatggaaaaa cggctttgcc gcggccctct cacttccctg  16440
ttaagtatct tcctggcatc ttccaggaaa tctccgcccc gttcgtaagc catttccgct  16500
cgccgcagtc gaacgaccga gcgtagcgag tcagtgagcg aggaagcgga atatatcctg  16560
tatcacatat tctgctgacg caccggtgca gccttttttc tcctgccaca tgaagcactt  16620
cactgacacc ctcatcagtg ccaacatagt aagccagtat acactccgct agcgccacgc  16680
gtatcgatga attcgttaat acgactcact ata                               16713
```

<210> SEQ ID NO 10
<211> LENGTH: 12572
<212> TYPE: RNA
<213> ORGANISM: Artificial Sequence
<220> FEATURE:
<223> OTHER INFORMATION: Hybrid BVD virus NADL890

<400> SEQUENCE: 10

```
guauacgaga auuagaaaag gcacucguau acguauuggg caauuaaaaa uaauaauuag     60
gccuagggaa caaaucccuc ucagcgaagg ccgaaaagag gcuagccaug cccuuaguag    120
gacuagcaua augagggggg uagcaacagu ggugaguucg uuggauggcu uaagcccuga    180
guacagggua gucgucagug guucgacgcc uuggaauaaa ggucucgaga ugccacgugg    240
acgagggcau gcccaaagca caucuuaacc ugagcggggg ucgcccaggu aaaagcaguu    300
uuaaccgacu guuacgaaua cagccugaua gggugcugca gaggcccacu guauugcuac    360
uaaaaaucuc ugcuguacau ggcacaugga guugaucaca aaugaacuuu uauacaaaac    420
auacaaacaa aaacccgucg ggguggagga accuguuuau gaucaggcag gugaucccuu    480
auuuggugaa aggggagcag uccacccuca aucgacgcua aagcucccac acaagagagg    540
ggaacgcgau guuccaacca acuuggcauc cuuaccaaaa agaggugacu gcaggucggg    600
uaauagcaga ggaccuguga gcgggaucua ccugaagcca gggccacuau uuuaccagga    660
cuauaaaggu cccgucuauc acagggcccc gcuggagcuc uuugaggagg gauccaugug    720
ugaaacgacu aaacggauag ggagaguaac uggaagugac ggaaagcugu accacauuua    780
```

-continued

```
uguguguaua gauggaugua uaauaauaaa aagugccacg agaaguuacc aaaggguguu    840
caggugggu c cauaauaggc uugacugccc ucuaugggu c acaaguugcu cagacacgaa    900
agaagaggga gcaacaaaaa agaaaacaca gaaacccgac agacuagaaa gggggaaaau    960
gaaaauagug cccaaagaau cugaaaaaga cagcaaaacu aaaccuccgg augcuacaau   1020
aguggu ggaa ggagucaaau accaggugag gaagaaggga aaaaccaaga guaaaaacac   1080
ucaggacggc uuguaccaua acaaaaacaa accucaggaa ucacgcaaga aacuggaaaa   1140
agcauuguug gcgugggcaa uaauagcuau aguuuuguuu caaguuacaa ugggagaaaa   1200
cauaacacag uggaaccuac aagauaaugg gacggaaggg auacaacggg caauguucca   1260
aaggggugug aauagaaguu uacauggaau cuggccagag aaaaucugua cuggcguccc   1320
uucccaucua gccaccgaua uagaacuaaa aacaauucau gguaugaugg augcaaguga   1380
gaagaccaac uacacguguu gcagacuuca acgccaugag uggaacaagc augguuggug   1440
caacugguac aauauugaac ccuggauucu agucaugaau agaacccaag ccaaucucac   1500
ugagggacaa ccaccaaggg agugcgcagu cacuuguagg uaugauaggg cuagugacuu   1560
aaacgu ggua acacaagcua gagauagccc cacacccuua acagguugca agaaaggaaa   1620
gaacuucucc uuugcaggca uauugaugcg ggccccugc aacuuugaaa uagcugcaag   1680
ugauguauua uucaaagaac augaacgcau uaguauguuc caggauacua cucuuuaccu   1740
uguugacggg uugaccaacu ccuuagaagg ugccagacaa ggaaccgcua aacugacaac   1800
cugguuaggc aagcagcucg ggauacuagg aaaaaaguug gaaaacaaga guaagacgug   1860
guuuggagca uacgcugcuu ccccuuacug ugauguggau cggaagaucg guuacgucug   1920
guauacaaaa aacugcacuc cagcuugccu cccaagaaac accaagauaa uaggccccgg   1980
gaaguuugac accaacgccg aagauggcaa aauacuccau gagaugggag ggcaccucuc   2040
agaauuugcc cuauuguccu ugguguucu gucugacuuu gccccagaaa ccgcgagugu   2100
caucuacuug guucuacauu uugcgauccc gcaaagccac guugauguag acacaugcga   2160
caagaaccag cugaauuuaa cggucgcaac uacaguagca gaagucauac cagggacagu   2220
guggaaccua gggaaguaug ucugcauaag accggacugg uggccauaug agacgacgac   2280
agucuucguc uuagaggaag cagggcaagu aaucaaauug ggcuaaggg ccaucagaga   2340
cuuaacuagg auauggaacg cugccaccac cacagcuuuc cuaaucuuuu uagugaaagc   2400
acugagggga caacuaaucc aagggcuauu guggcugaug cuaauaacag gagcucaggg   2460
cuucccugaa ugcaaggagg gcuuccaaua ugccauaucg aaagacagaa aaaugggguu   2520
auuggggcca gagagcuuaa cuacaacaug gcaccguccc acaaaaaaau uaguggacuc   2580
caugguacaa guauggugug aaggaaaaga cuugaaaaua uuaaaaacgu gccccaagga   2640
agagagguac cuaguggcug ugcacgagag agcccuauca accagugcug aguuuaugcc   2700
aaucagugau gggacaauag gcccagaugu gauagauaug ccugaugacu uugaguuugg   2760
acucugcccu ugugacgcaa aaccagugau aaagggcaaa uuuaaugcca gcuuacugaa   2820
uggaccagcu uuccagaugg uaugcccaca ggggguggacu gguacaauag aaugcacccu   2880
ggcgaaccaa gacaccuuag acacaacugu gguuaggaca uacagaagaa cuacuccauu   2940
ucagcggaga aaauggugcu ccuaugaaaa aauaauaggg gaagauaucc augaaugcau   3000
ucugggugga aacuggacau gcauaacugg ugaccauagc aaguugaaag acggaccuau   3060
caagaaaugu aaguggugug gcuaugacuu cgucaacuca gagggacugc cacacuaccc   3120
aauagguaag ugcaugcuca ucaaugagag uggguacagg uauguagaug acaccucuug   3180
```

-continued cgauaggggu gguguagcca uagucccaac aggcaccgua aaguguagaa uaggugacgu 3240
cacggugcag guugucgcuu cuaauaauga ucugggaccc augcccugca gcccagcuga 3300
agugauagca agugaaggac caguggaaaa gacugcaugc acauuuaacu auucaaggac 3360
acuacccaau aaguauuaug agccaaggga ccguuacuuc caacaauaca ugcuaaaagg 3420
ggaguggcaa uauugguuug accuggauca uguagaccac cacaaagacu acuucucaga 3480
guucauaauc auagcagugg ucgccuuguu ggguggcaga uauguacuuu gguuacuggu 3540
uacauacaug gucuuaucag aacagaaggc cuuagggauu caguauggau caggggaagu 3600
ggugaugaug ggcaacuugc uaacccauaa caauauugaa guggugacau acuucuugcu 3660
gcuguaccua cugcugaggg aggagagcgu aaagaagugg gucuuacucu uauaccacau 3720
cuuaguggua cacccaauca aaucuguaau ugugauccua cugaugauug gggaugugguu 3780 aaaggccgau ucaggggggcc aagaguacuu ggggaaaaua gaccucuguu uuacaacagu 3840
aguacuaauc gucauagguu uaaucauagc caggcgugac ccaacuauag ugccacuggu 3900
aacaauaaug gcagcacuga gggucacuga acugacccac cagccuggag uugacaucgc 3960
uguggcgguc augacuauaa cccuacugau gguuagcuau gugacagauu auuuuagaua 4020
uaaaaaaugg uuacagugca uucucagccu gguaucuggg guguucuuga uaagaagccu 4080
aauauaccua gguagaaucg agaugccaga gguaacuauc ccaaacugga gaccacuaac 4140
uuuaauacua uuauauuuga ucucaacaac aauuguaacg agguggaagg uugacguggc 4200
uggccuauug uugcaaugug ugccuaucuu auugcugguc acaaccuugu gggccgacuu 4260
cuuaacccua auacugaucc ugccuaccua ugaauugguu aaauuauacu aucugaaaac 4320
uguuaggacu gauauagaaa gaaguuggcu aggggggaua gacuauacaa gaguugacuc 4380
caucuacgac guugaugaga guggagaggg cguauaucuu uuuccaucaa ggcagaaagc 4440
acaggggaau uuuucuauac ucuugccccu uaucaaagca acacugauaa guugcgucag 4500
caguaaaugg cagcuaauau acaugaguua cuuaacuuug gacuuuaugu acuacaugca 4560
caggaaaguu auagaagaga ucucaggagg uaccaacaua auauccaggu uaguggcagc 4620
acucauagag cugaacuggu ccauggaaga agaggagagc aaaggcuuaa agaaguuuua 4680
ucuauugucu ggaagguuga gaaaccuaau aauaaaacau aagguaagga augagaccgu 4740
ggcuucuugg uacggggagg aggaagucua cgguaugcca aagaucauga cuauaaucaa 4800
ggccaguaca cugaguaaga gcaggcacug cauaauaugc acuguaugug agggccgaga 4860 gugggaaaggu ggcaccugcc caaaaugugg acgccauggg aagccgauaa cgugugggau 4920
gucgcuagca gauuucgaag aaagacacua uaaaagaauc uuuauaaggg aaggcaacuu 4980
ugaggguaug ugcagccgau gccagggaaa gcauaggagg uuugaaaugg accgggaacc 5040
uaagagugcc agauacugug cugaguguaa uaggcugcau ccugcugagg aaggugacuu 5100
uugggcagag ucgagcaugu ugggccucaa aaucaccuac uuugcgcuga uggauggaaa 5160 ggguguaugau aucacagagu gggcuggaug ccagcgugug ggaaucuccc cagauaccca 5220
cagaguccuu ugucacaucu cauuugguuc acggaugccu uucaggcagg aauacaaugg 5280
cuuuguacaa uauaccgcua gggggcaacu auuucugaga aacuugcccg uacuggcaac 5340
uaaaguaaaa augcucaugg uaggcaaccu uggagaagaa auugguaauc uggaacaucu 5400
uggguggauc cuaagggggc cugccgugug uaagaagauc acagagcacg aaaaaugcca 5460
cauuaauaua cuggauaaac uaaccgcauu uuucgggauc augccaaggg ggacuacacc 5520

-continued

```
cagagccccg gugagguucc cuacgagcuu acuaaaagug aggaggggguc uggagacugg   5580
cugggcuuac acacaccaag gcgggauaag uucagucgac cauguaaccg ccggaaaaga   5640
ucuacugguc ugugacagca ugggacgaac uagagugguu ugccaaagca acaacagguu   5700
gaccgaugag acagaguaug gcgucaagac ugacucaggg ugcccagacg gugccagaug   5760
uuauguguua aauccagagg ccguuaacau aucaggaucc aaaggggcag ucguucaccu   5820
ccaaaagaca gguggagaau ucacgugugu caccgcauca ggcacaccgg cuuucuucga   5880
ccuaaaaaac uugaaaggau ggucaggcuu gccuauauuu gaagccucca gcgggagggu   5940
gguuggcaga gucaaaguag ggaagaauga agagucuaaa ccuacaaaaa uaaugagugg   6000
aauccagacc gucucaaaaa acacagcaga ccugaccgag auggucaaga agauaaccag   6060
caugaacagg ggagacuuca agcagauuac uuuggcaaca ggggcaggca aaaccacaga   6120
acucccaaaa gcaguuauag aggagauagg aagacacaag agaguauuag uucuuauacc   6180
auuaagggca gcggcagagu cagucuacca guauaugaga uugaaacacc caagcaucuc   6240
uuuuaaccua aggauagggg acaugaaaga gggggacaug gcaaccggga uaaccuaugc   6300
aucauacggg uacuucugcc aaaugccuca accaaagcuc agagcugcua ugguagaaua   6360
cucauacaua uucuuagaug aauaccauug ugccacuccu gaacaacugg caauuaucgg   6420
gaagauccac agauuuucag agaguauaag gguugucgcc augacugcca cgccagcagg   6480
gucggugacc acaacagguc aaaagcaccc aauagaggaa uucauagccc ccgagguaau   6540
gaaaggggag gaucuuggua gucaguuccu ugauauagca ggguuaaaaa uaccagugga   6600
ugagaugaaa ggcaauaugu ugguuuuugu accaacgaga aacauggcag uagagguagc   6660
aaagaagcua aaagcuaagg gcuauaacuc uggauacuau uacaguggag aggauccagc   6720
caaucugaga guugugacau cacaaucccc cuauguaauc guggcuacaa augcuauuga   6780
aucaggagug acacuaccag auuuggacac gguuauagac acgggguuga aaugugaaaa   6840
gagggugagg guaucaucaa agauacccuu caucguaaca ggccuuaaga ggauggccgu   6900
gacugugggu gagcaggcgc agcguagggg cagaguaggu agagugaaac ccgggaggua   6960
uuauaggagc caggaaacag caacaggguc aaaggacuac cacuaugacc ucuugcaggc   7020
acaaagauac gggauugagg auggaaucaa cgugacgaaa uccuuuaggg agaugaauua   7080
cgauuggagc cuauacgagg aggacagccu acuaauaacc cagcuggaaa uacuaaauaa   7140
ucuacucauc ucagaagacu ugccagccgc uguuaagaac auaauggcca ggacugauca   7200
cccagagcca auccaacuug cauacaacag cuaugaaguc cagguccegg uccuauuccc   7260
aaaaauaagg aauggagaag ucacagacac cuacgaaaau uacucguuuc uaaaugccag   7320
aaaguuaggg gaggaugugc ccguguauau cuacgcuacu gaagaugagg aucuggcagu   7380
ugaccucuua gggcuagacu ggccugaucc ugggaaccag cagguagugg agacugguaa   7440
agcacugaag caagugaccg gguuguccuc ggcugaaaau gcccuacuag uggcuuuauu   7500
uggguaugug gguuaccagg cucucucaaa gaggcauguc ccaaugauaa cagacauaua   7560
uaccaucgag gaccagagac uagaagacac cacccaccuc caguaugcac ccaacgccau   7620
aaaaaccgau gggacagaga cugaacugaa agaacuggcg ucgggugacg uggaaaaaau   7680
caugggagcc auuucagauu augcagcugg gggacuggag uuuguuaaau cccaagcaga   7740
aaagauaaaa acagcuccuu uguuuaaaga aaacgcagaa gccgcaaaag gguaugucca   7800
aaaauucauu gacucauuaa uugaaaauaa agaagaaaua aucagauaug guuuguggggg   7860
aacacacaca gcacuauaca aaagcauagc ugcaagacug ggcaugaaa cagcguuugc   7920
```

-continued

```
cacacuagug uuaaaguggc uagcuuuugg aggggaauca gugucagacc acgucaagca   7980
ggcggcaguu gauuuagugg ucuauuaugu gaugaauaag ccuuccuucc caggugacuc   8040
cgagacacag caagaaggga ggcgauucgu cgcaagccug uucaucuccg cacuggcaac   8100
cuacacauac aaaacuugga auuaccacaa ucucucuaaa gugguggaac cagcccuggc   8160
uuaccucccc uaugcuacca gcgcauuaaa aauguucacc ccaacgcggc uggagagcgu   8220
ggugauacug agcaccacga uauauaaaac auaccucucu auaaggaagg ggaagaguga   8280
uggauugcug gguacgggga uaagugcagc cauggaaauc cugucacaaa acccaguauc   8340
gguagguaua ucugugaugu ugggguaggg ggcaaucgcu gcgcacaacg cuauugaguc   8400
cagugaacag aaaaggaccc uacuuaugaa gguguuugua aagaacuucu uggaucaggc   8460
ugcaacagau gagcugguaa aagaaaaccc agaaaaaauu auaauggccu uauuugaagc   8520
aguccagaca auugguaacc cccugagacu aauauaccac cuguaugggg uuuacuacaa   8580
agguugggag gccaaggaac uaucugagag gacagcaggc agaaacuuau ucacauugau   8640
aauguuugaa gccuucgagu uauuagggau ggacucacaa gggaaaauaa ggaaccuguc   8700
cggaaauuac auuuuggauu ugauauacgg ccuacacaag caaaucaaca gagggcugaa   8760
gaaaauggua cuggggug gg ccccugcacc cuuuaguugu gacuggaccc cuagugacga   8820
gaggaucaga uugccaacag acaacuauuu gaggguagaa accaggugcc cauguggcua   8880
ugagaugaaa gcuuucaaaa auguaggugg caaacuuacc aaaguggagg agagcgggcc   8940
uuuccuaugu agaaacagac cugguagggg accagucaac uacagaguca ccaaguauua   9000
cgaugacaac cucagagaga uaaaaccagu agcaaaguug gaaggacagg uagagcacua   9060
cuacaaaggg gucacagcaa aaauugacua caguaaagga aaaaugcucu uggccacuga   9120
caagugggag gugg aacaug gugucauaac cagguuagcu aagagauaua cuggggucgg   9180
guucaauggu gcauacuuag gugacgagcc caaucaccgu gcucuagugg agagggacug   9240
ugcaacuaua accaaaaaca caguacaguu ucuaaaaaug aagaaggggu gugcguucac   9300
cuaugaccug accaucucca aucugaccag gcucaucgaa cuaguacaca ggaacaaucu   9360
ugaagagaag gaaauaccca ccgcuacggu caccacaugg cuagcuuaca ccuucgugaa   9420
ugaagacgua gggacuauaa aaccaguacu aggagagaga guaaucccg acccuguagu   9480
ugauaucaau uuacaaccag aggugcaagu ggacacguca gagguuggga ucacaauaau   9540
uggaagggaa acccugauga caacgggagu gacaccuguc uuggaaaaag uagagccuga   9600
cgccagcgac aaccaaaacu cggugaagau cgggguuggau gaggguaauu acccagggcc   9660
uggaauacag acacauacac uaacagaaga aauacacaac agggaugcga ggcccuucau   9720
caugauccug ggcucaagga auuccauauc aaauagggca aagacugcua gaaauauaaa   9780
ucuguacaca ggaaaugacc ccagggaaau acgagacuug auggcugcag ggcgcauguu   9840
aguaguagca cugagggaug ucgacccuga gcugucugaa auggucgauu ucaaggggac   9900
uuuuuuagau agggaggccc uggaggcucu aagucucggg caaccuaaac cgaagcaggu   9960
uaccaaggaa gcuguuagga auuugauaga acagaaaaaa gauguggaga ucccuaacug  10020
guuugcauca gaugacccag uauuucugga aguggccuua aaaaaugaua aguacuacuu  10080
aguaggagau guuggagagc uaaaagauca agcuaaagca cuuggggcca cggaucagac  10140
aagaauuaua aaggagguag gcucaaggac guaugccaug aagcuaucua gcugguuccu  10200
caaggcauca aacaaacaga ugaguuuaac uccacuguuu gaggaauugu ugcuacggug  10260
```

-continued

```
cccaccugca acuaagagca auaaggggca cauggcauca gcuuaccaau uggcacaggg  10320
uaacugggag ccccucgguu gcggggugca ccuagguaca auaccagcca gaagggugaa  10380
gauacaccca uaugaagcuu accugaaguu gaaagauuuc auagaagaag aagagaagaa  10440
accuaggguu aaggauacag uaauaagaga gcacaacaaa uggauacuua aaaaaauaag  10500
guuucaagga aaccucaaca ccaagaaaau gcucaaccca gggaaacuau cugaacaguu  10560
ggacagggag gggcgcaaga ggaacaucua caaccaccag auugguacua uaaugucaag  10620
ugcaggcaua aggcuggaga aauugccaau agugagggcc caaaccgaca ccaaaaccuu  10680
ucaugaggca auaagagaua agauagacaa gagugaaaac cggcaaaauc cagaauugca  10740
caacaaauug uuggagauuu uccacacgau agcccaaccc acccugaaac acaccuacgg  10800
ugaggugacg ugggagcaac uugaggcggg gguaaauaga aaggggcag caggcuuccu  10860
ggagaagaag aacaucggag aaguauugga uucagaaaag caccugguag aacaauuggu  10920
cagggaucug aaggccggga gaaagauaaa auauuaugaa acugcaauac caaaaaauga  10980
gaagagagau gucagugaug acuggcaggc aggggaccug gugguugaga agaggccaag  11040
aguuauccaa uacccugaag ccaagacaag gcuagccauc acuaagguca uguauaacug  11100
ggugaaacag cagcccguug ugauuccagg auaugaagga aagacccccu uguucaacau  11160
cuuugauaaa gugagaaagg aaugggacuc guucaaugag ccaguggccg uaaguuuuga  11220
caccaaagcc ugggacacuc aagugacuag uaaggaucug caacuuauug gagaaaucca  11280
gaaauauuac uauaagaagg aguggcacaa guucauugac accaucaccg accacaugac  11340
agaaguacca guuauaacag cagaugguga aguauauaua agaaaugggc agagagggag  11400
cggccagcca gacacaagug cuggcaacag cauguuaaau guccugacaa ugauguacgg  11460
cuucugcgaa agcacagggg uaccguacaa gaguuucaac aggguggcaa ggauccacgu  11520
cugugggau gauggcuucu uaauaacuga aaaagguua gggcugaaau uugcuaacaa  11580
agggaugcag auucuucaug aagcaggcaa accucagaag auaacggaag gggaaaagau  11640
gaaaguugcc uauagauuug aggauauaga guucuguucu cauaccccag ucccuguuag  11700
gugguccgac aacaccagua gucacauggc cgggagagac accgcuguga uacuaucaaa  11760
gauggcaaca agauuggauu caaguggaga gaggggguacc acagcauaug aaaaagcggu  11820
agccuucagu uucuugcuga uguauuccug gaacccgcuu guuaggagga uuugccuguu  11880
gguccuuucg caacagccag agacagaccc aucaaaacau gccacuuauu auuacaaagg  11940
ugauccaaua ggggccuaua aagauguaau aggucggaau cuaagugaac ugaagagaac  12000
aggcuuugag aaauuggcaa aucuaaaccu aagccugucc acguuggggg ucuggacuaa  12060
gcacacaagc aaaagaauaa uucaggacug uguugccauu gggaaagaag agggcaacug  12120
gcuaguuaag cccgacaggc ugauauccag caaaacuggc cacuuauaca uaccugauaa  12180
aggcuuuaca uuacaaggaa agcauuauga gcaacugcag cuaagaacag agacaaaccc  12240
ggucaugggg guugggacug agagauacaa guuagguccc auagucaauc ugcugcugag  12300
aagguugaaa auucugcuca ugacggccgu cggcgucagc agcugagaca aaauguauau  12360
auuguaaaua aauuaaucca uguacauagu guauauaaau auaguuggga ccguccaccu  12420
caagaagacg acacgcccaa cacgcacagc uaaacaguag ucaagauuau cuaccucaag  12480
auaacacuac auuuaaugca cacagcacuu uagcuguaug aggauacgcc cgacgucuau  12540
aguuggacua gggaagaccu cuaacagccc cc                                  12572
```

-continued

<210> SEQ ID NO 11
<211> LENGTH: 1606
<212> TYPE: RNA
<213> ORGANISM: Artificial Sequence
<220> FEATURE:
<223> OTHER INFORMATION: PCR fragment

<400> SEQUENCE: 11
gaagaucggu uacgucuggu auacaaaaaa cugcacucca gcuugccucc caagaaacac 60
caagauaaua ggccccggga aguuugacac caacgccgaa gauggcaaaa uacuccauga 120
gaugggaggg caccucucag aauuugcccu auuguccuug gugguucugu cugacuuugc 180
cccagaaacc gcgaguguca ucuacuuggu ucuacauuuu gcgaucccgc aaagccacgu 240
ugauguagac acaugcgaca agaaccagcu gaauuuaacg gucgcaacua caguagcaga 300
agucauacca gggacagugu ggaaccuagg gaaguauguc ugcauaagac cggacuggug 360
gccauaugag acgacgacag ucuucgucuu agaggaagca gggcaaguaa ucaaauuggg 420
gcuaagggcc aucagagacu uaacuaggau auggaacgcu gccaccacca cagcuuuccu 480
aaucuuuuua gugaaagcac ugaggggaca acuaauccaa gggcuauugu ggcugaugcu 540
aauaacagga gcucagggcu ucccugaaug caaggagggc uuccaauaug ccauaucgaa 600
agacagaaaa auggggguuau uggggccaga gagcuuaacu acaacauggc accgucccac 660
aaaaaaauua guggacucca ugguacaagu augguguga ggaaaagacu ugaaaauauu 720
aaaaacgugc cccaaggaag agagguaccu aguggcugug cacgagagag cccuaucaac 780
cagugcugag uuuaugccaa ucagugaugg gacaauaggc ccagauguga uagauaugcc 840
ugaugacuuu gaguuuggac ucugcccuug ugacgcaaaa ccagugauaa agggcaaauu 900
uaaugccagc uuacugaaug gaccagcuuu ccagauggua ugcccacagg gguggacugg 960
uacaauagaa ugcacccugg cgaaccaaga caccuuagac acaacugugg uuaggacaua 1020
cagaagaacu acuccauuuc agcggagaaa auggugcucc uaugaaaaaa uaauagggga 1080
agauauccau gaaugcauuc ugggugugaaa cuggacaugc auaacuggug accauagcaa 1140
guugaaagac ggaccuauca agaaauguaa guggugugggc uaugacuucg ucaacucaga 1200
gggacugcca cacuacccaa uagguaagug caugcucauc aaugagagug gguacaggua 1260
uguagaugac accucuugcg auaggggugg uguagccaua gucccaacag gcaccguaaa 1320
guguagaaua ggugacguca cggugcaggu ugucgcuucu aauaaugauc ugggacccau 1380
gcccugcagc ccagcugaag ugauagcaag ugaaggacca guggaaaaga cugcaugcac 1440
auuuaacuau ucaaggacac uacccaauaa guauuaugag ccaagggacc guuacuucca 1500
acaauacaug cuaaaagggg aguggcaaua uugguuugac cuggaucaug uagaccacca 1560
caaagacuac uucucagagu ucauaaucau agcagugguc gccuug 1606

<210> SEQ ID NO 12
<211> LENGTH: 1612
<212> TYPE: RNA
<213> ORGANISM: Artificial Sequence
<220> FEATURE:
<223> OTHER INFORMATION: PCR fragment

<400> SEQUENCE: 12
caaaauuggc uacauauggu auacaaaaaa uugcaccccu gccugcuuac ccaagaacac 60
aaaaauuguc ggcccuggga aauuugacac caaugcagag gacggcaaga uauuacauga 120 gaugggggu cacuugucgg agguacuacu acuuucuuua guggugcugu ccgacuucgc 180

-continued

```
accggaaaca gcuaguguaa uguaccuaau ccuacauuuu uccaucccac aaagucacgu    240

ugauguaaug gauugugaua agacccaguu gaaccucaca guggagcuga caacagcuga    300

aguaauacca gggucggucu ggaaucuagg caaauaugua uguauaagac caaauuggug    360

gccuuaugag acaacuguag uguuggcauu ugaagaggug agccaggugg ugaaguuagu    420

guugagggca cucagagauu uaacacgcau uuggaacgcu gcaacaacua cugcuuuuuu    480

aguaugccuu guuaagauag ucaggggcca gaugguacag ggcauucugu ggcuacuauu    540

gauaacaggg guacaagggc acuuggauug caaaccugaa uucucguaug ccauagcaaa    600

ggacgaaaga auuggucaac ugggggcuga aggccuuacc accacuugga aggaauacuc    660

accuggaaug aagcuggaag acacaauggu cauugcuugg ugcgaagaug ggaaguuaau    720

guaccuccaa agaugcacga gagaaaccag auaucucgca aucuugcaua caagagccuu    780

gccgaccagu gugguauuca aaaaacucuu ugaugggcga aagcaagagg auguagucga    840

aaugaacgac aacuuugaau uuggacucug cccaugugau gccaaaccca uaguaagagg    900

gaaguucaau acaacgcugc ugaacggacc ggccuuccag augguaugcc ccauaggaug    960

gacagggacu guaagcugua cgucauucaa uauggacacc uuagccacaa cugugguacg   1020

gacauauaga aggucuaaac cauucccuca uaggcaaggc uguaucaccc aaaagaaucu   1080

gggggaggau cuccauaacu gcauccuugg aggaaauugg acuugugugc cuggagacca   1140

acuacuauac aaagggggcu cuauugaauc uugcaagugg uguggcuauc aauuuaaaga   1200

gagugaggga cuaccacacu accccauugg caaguguaaa uuggagaacg agacugguua   1260

caggcuagua gacaguaccu cuugcaauag agaaggugug gccauaguac cacaagggac   1320

auuaaagugc aagauaggaa aaacaacugu acaggucaua gcuauggaua ccaaacucgg   1380

accuaugccu ugcagaccau augaaaucau aucaagugag gggccuguag aaaagacagc   1440

guguacuuuc aacuacacua agacauuaaa aaauaaguau uuugagccca gagacagcua   1500

cuuucagcaa uacaugcuaa aaggagagua ucaauacugg uuugaccugg aggugacuga   1560

ccaucaccgg gauuacuucg cugaguccau auuaguggug guaguagccc uc           1612
```

GENERATION OF TYPE I/TYPE II HYBRID FORM OF BOVINE VIRAL DIARRHEA VIRUS FOR USE AS VACCINE

CROSS-REFERENCE TO RELATED APPLICATION

This application claims the benefit of U.S. Provisional Patent Application No. 60/315,445 filed Aug. 28, 2001, the contents of which are hereby incorporated by reference in its entirety.

FIELD OF THE INVENTION

The present invention relates to genetically engineered type I/type II hybrid BVDV viruses. The hybrid viruses, as well as the hybrid viral genome, can be used in vaccines for protecting cattle from BVDV infection.

BACKGROUND OF THE INVENTION

Bovine viral diarrhea (BVD) virus is classified in the pestivirus genus and Flaviviridae family. It is closely related to viruses causing border disease in sheep and classical swine fever. Infected cattle exhibit "mucosal disease" which is characterized by elevated temperature, diarrhea, coughing and ulcerations of the alimentary mucosa (Olafson, et al., *Cornell Vet.* 36:205–213 (1946); Ramsey, et al., *North Am. Vet.* 34:629–633 (1953)). The BVD virus is capable of crossing the placenta of pregnant cattle and may result in the birth of persistently infected (PI) calves (Malmquist, *J. Am. Vet. Med. Assoc.* 152:763–768 (1968); Ross, et al., *J. Am. Vet Med. Assoc.* 188:618–619 (1986)). These calves are immunotolerant to the virus and persistently viremic for the rest of their lives. They provide a source for outbreaks of mucosal disease (Liess, et al., *Dtsch. Tieraerztl. Wschr.* 81:481–487 (1974)) and are highly predisposed to infection with microorganisms causing diseases such as pneumonia or enteric disease (Barber, et al., *Vet. Rec.* 117:459–464 (1985)).

According to virus growth in cultured cells, two viral biotypes have been classified: viruses that induce a cytopathic effect (cp) and viruses that do not induce a cytopathic effect (ncp) in infected cells (Lee et al., *Am. J. Vet. Res.* 18: 952–953; Gillespie et al., *Cornell Vet.* 50: 73–79, 1960). Cp variants can arise from the PI animals preinfected with ncp viruses (Howard et al., *Vet. Microbiol.* 13: 361–369, 1987; Corapi et al., *J. Virol.* 62: 2823–2827, 1988). Based on the genetic diversity of the 5' non-translated-region (NTR) and the antigenic differences in the virion surface glycoprotein E2 of BVD viruses, two major genotypes have been proposed: type I and II. BVDV type 1 represents classical or traditional virus strains which usually produce only mild diarrhoea in immunocompetent animals, whereas BVDV type 2 are emerging viruses with high virulence which can produce thrombocytopenia, hemorrhages and acute fatal disease (Corapi et al., *J. Virol.* 63: 3934–3943; Bolin et al., *Am. J. Vet Res.* 53: 2157–2163; Pellerin et al., *Virology* 203: 260–268, 1994; Ridpath et al., *Virology* 205: 66–74, 1994; Carman et al., *J. Vet. Diagn. Invest.* 10: 27–35, 1998). Type I and II viruses have distinct antigenicity determined by a panel of MAbs and by cross-neutralization using virus-specific antisera raised in animals (Corapi et al., *Am. J. Vet. Res.* 51: 1388–1394, 1990). Viruses of either genotype may exist as one of the two biotypes, cp or ncp virus.

The RNA genome of BVDV is approximately 12.5 kb in length and contains a single open reading frame located between the 5' and 3' NTRs (Collett et al., *Virology* 165: 191–199). A polyprotein of approximately 438 kD is translated from the open reading frame and is processed into viral structural and nonstructural proteins via cellular and viral protease (Wiskerchen et al., *Virology* 184: 341–350, 1991; Ruemenapf et al., *J. Virol* 67: 3288–3294, 1993; Elbers et al., *J. Virol.* 70: 4131–4135, 1996; Tautz et al., *J. Virol* 71: 5415–5422, 1997; Xu et al., *J. Virol* 71: 5312–5322, 1997).

The first viral protein encoded by the open reading frame is a protease $N^{pro}$ which cleaves its self from the rest of the polyprotein (Wiskerchen et al., *J. Virol* 65: 4508–4514, 1991; Stark et al., *J. Virol.* 67: 7088–7095, 1993). The second protein C is the structural core protein, which packages the genomic RNA and forms the viral virion (Thiel et al., *J. Virol.* 67: 3288–3294, 1993). Following the protein C-coding sequence are three sequences coding for envelope proteins E0, E1 and E2. E0, E1 and E2 are all glycoproteins. E2 is very antigenic and elicits the production of neutralizing antibodies in the host after infection or vaccination with live or killed vaccines.

A small peptide p7 is located between E2 and the nonstructural proteins. Following p7 is the p125 or NS23 region. NS2 is highly hydrophobic and has a zinc finger motif. NS3 is hydrophilic and is a marker of cytopathic BVDV. NS3 is the most conserved protein in the genus pestivirus and highly immunogenic in infected cells. Replication of a ncp virus in infected animal can convert the virus into the cp biotype through genetic recombination event by insertion of an extra viral or cellular RNA sequence between NS2 and NS3 coding region. As a consequence of the recombination, p125 is processed and free NS2 and NS3 proteins are released (Meyers et al., *Nature* 341: 491, 1989*; Virology* 180: 602–616, 1991*; Virology* 191: 368–386, 1992; Tautz et al., *J. Virol.* 68: 3289–3297, 1994). NS3 is a viral protease responsible for most of the nonstructural protein processing (Wiskerchen et al., *Virology* 184: 341–350, 1991). It is also proposed that NS3 plays an essential role in viral RNA replication because of its RNA-stimulated NTPase activity and RNA helicase activity (Tamura et al., *Virology* 193: 1–10, 1993; Warrener et al., *J. Virol.* 69: 1720–1726, 1995; Grassmann et al., *J. Virol.* 73: 9196–9205, 1999). NS4A is located next to NS3 and is known as a cofactor for NS3 protease activity (Xu et al., *J. Virol.* 71: 5312–5322, 1997). Following NS4A are two viral proteins NS4B and NS5A with unknown functions. The last protein from the open-reading frame of the virus is NS5B, which is a RNA-dependent RNA polymerase and is responsible for viral RNA replication (Young et al., Ogram et al., *Fifth International Symposium on Positive Strand RNA Viruses* P2–15, P2–16, 1998).

Studies from BVD virus infected animals suggest that BVD viruses induce both B-cell and T-cell responses in animals (Donis et al., *Virology* 158: 168–173, 1987; Larsson et al., *Vet. Microbiol.* 31: 317–325, 1992; Howard et al., *Vet. Immunol. Immunopathol.* 32: 303–314, 1992; Lambot et al., *J. Gen. Virol.* 78: 1041–1047, 1997; Beer et al., *Vet. Microbiology.* 58: 9–22, 1997). Both antibodies (Bolin et al., *Am. J. Vet. Res.* 51: 703–707, 1990).

A number of BVDV vaccines have been developed using chemically inactivated BVD viral isolates (Fernelius et al., *Am. J. Vet. Res.* 33: 1421–1431, 1972; Kolar et al., *Am. J. Vet. Res.* 33: 1415–1420, 1972; McClurkin et al., *Arch. Virol.* 58: 119, 1978). Multiple doses are required for the inactivated viral vaccines to achieve primary immunization. Some inactivated BVDV vaccines provide protection against infection by type I BVDV only (Beer et al., Vet. Microbiology. 77:195–208, 2000). Fetal protection has not been achieved with inactivated BVDV vaccines due to a short duration of immunity and an inefficient cross-type protection (Bolin, *Vet. Clin. North Am. Food Anim. Pract.* 11: 615–625, 1995).

Modified-live virus (MLV) vaccine, on the other hand, offers a higher level of protection. Currently, licensed BVDV mlv vaccines are produced using attenuated viruses obtained via repeated passage in bovine or porcine cells (Coggins et al., *Cornell Vet* 51: 539, 1961; Phillips et al., *Am. J. Vet. Res.* 36: 135-, 1975), or using chemically modified viruses which exhibit temperature-sensitive phenotype (Lobmann et al., Am. J. Vet. Res. 45: 2498-, 1984; 47: 557–561, 1986). A single dose of MLV vaccine is sufficient for immunization, and duration of the immunity can last for years in vaccinated cattle. However, as these vaccines have been developed using type I BVDV virus strains, the full protection is achieved only for type I virus.

There is a need for development of BVDV vaccines that provide protection against both type I and type II viruses. Currently, there are ncp-BVD type II viruses which are candidates for use as an inactivated vaccine based on type II virus isolates (Flores et al., Vet. Microbiology, 77: 175–183, 2000).

The present invention provides genetically engineered type I/type II hybrid viruses using recombinant DNA technology. The present invention further provides immunogenic compositions and vaccines formulated using the genetically engineered hybrid viruses.

SUMMARY OF THE INVENTION

One embodiment of the present invention provides genetically engineered type I/type II hybrid BVD viruses having a hybrid genome derived by substituting a portion of the genome of a type I BVD virus with the corresponding portion of the genome of a type II BVD virus.

In a preferred embodiment, the present invention provides hybrid viruses carrying a genome derived from the genome of NADL (a type I BVD virus, deposited with the American Type Culture Collection and designated as VR-534) wherein at least a portion of the E1-E2 region of the NADL genome is replaced with the corresponding portion of the E1-E2 region of the genome of 890 (a known type II BVD virus).

A particularly preferred hybrid BVD virus of the present invention is NADL890, the genomic sequence of which is set forth in SEQ ID NO: 10. Viruses having a genomic sequence substantially the same as SEQ ID NO: 10 are also encompassed by the present invention.

Another embodiment of the present invention is directed to isolated genomic nucleic molecules of the hybrid BVD viruses described herein. Nucleic acid molecules as used herein encompass both RNA and DNA. A preferred nucleic acid molecule of the present invention is set forth in SEQ ID NO: 10. SEQ ID NO: 10 encompasses nucleotides 1–12572 of SEQ ID NO: 9. Nucleic acid molecules substantially the same as SEQ ID NO: 10 are also encompassed by the present invention.

In another embodiment, the present invention provides vectors carrying the genomic sequence of any one of the hybrid BVD viruses described herein. A preferred vector is pNADL890 (SEQ ID NO: 9) deposited with the American Type Culture Collection and designated as ATTC NO. PTA-3098, in which the genomic sequence of NADL890 (SEQ ID NO: 10) has been inserted.

Still another embodiment of the present invention is directed to host cells into which the genomic nucleic acid molecule of a hybrid BVD virus of the present invention has been introduced. "Host cells" as used herein include both prokaryotic and eukaryotic cells.

One embodiment of the present invention provides immunogenic compositions which include one or more of the hybrid BVD viruses of the present invention. A preferred attenuated BVD virus to be included in an immunogenic composition of the present invention is NADL890. Alternatively, the immunogenic compositions of the present invention can include genomic nucleic acid molecules of one or more of the hybrid BVD viruses of the present invention.

Another embodiment of the present invention provides methods of inducing an immune response against BVDV in an animal subject by administering an effective amount of an immunogenic composition of the present invention. The immune response induced may be directed to type II BVD viruses, or preferably to both type I and type II BDV viruses. "Animal subjects" as used herein include any animal that is susceptible to BVDV infections, such as bovine, sheep and swine.

In still another embodiment, the present invention provides vaccine compositions which include one or more of the hybrid BVD viruses of the present invention, preferably NADL890. Alternatively, the vaccine compositions can include the genomic nucleic acid molecules of one or more of the hybrid BVD viruses of the present invention.

In another embodiment, the present invention provides methods of treating BVDV infections in animal subjects by administering to an animal, a therapeutically effective amount of a hybrid BVD virus of the present invention. By "treating" is meant preventing or reducing the risk of infection by a virulent type II BVD virus, preferably, infection by both a virulent type II and a type I BVD virus, ameliorating the symptoms of an infection, or accelerating the recovery from an infection.

A further aspect of the present invention is directed to methods of determining the origin of a BVD virus in an animal subject, e.g., to determine the BDV virus in an animal as the hybrid virus of a prior vaccination. The determination can be made based on identifying a hybrid virus by the genomic and/or the protein composition of the hybrid virus.

In another embodiment, the present invention provides a method of modifying a genome of an isolated wild type BVD virus of type I to make it suitable for use in an immunogenic composition or a vaccine against both type I and type II BVD viruses. The method involves substituting a portion of the genome of the type I virus with the corresponding portion of the genome of a type II virus. Preferably, the E1–E2 region of the genome of a type I virus is replaced with the corresponding E1–E2 region of the genome of a type II virus.

BRIEF DESCRIPTION OF THE DRAWINGS

FIG. 3 shows the sequence of pNADL890.

FIG. 4 shows phenotypes of cells infection with NADL viruses, 890 viruses and NADL890 viruses. Pictures were taken at 24 hr post-infection.

FIG. 5 depicts the titers of antibodies in the serum from cattle infected with various strains of BVDV.

DETAILED DESCRIPTION OF THE INVENTION

Figure 1:
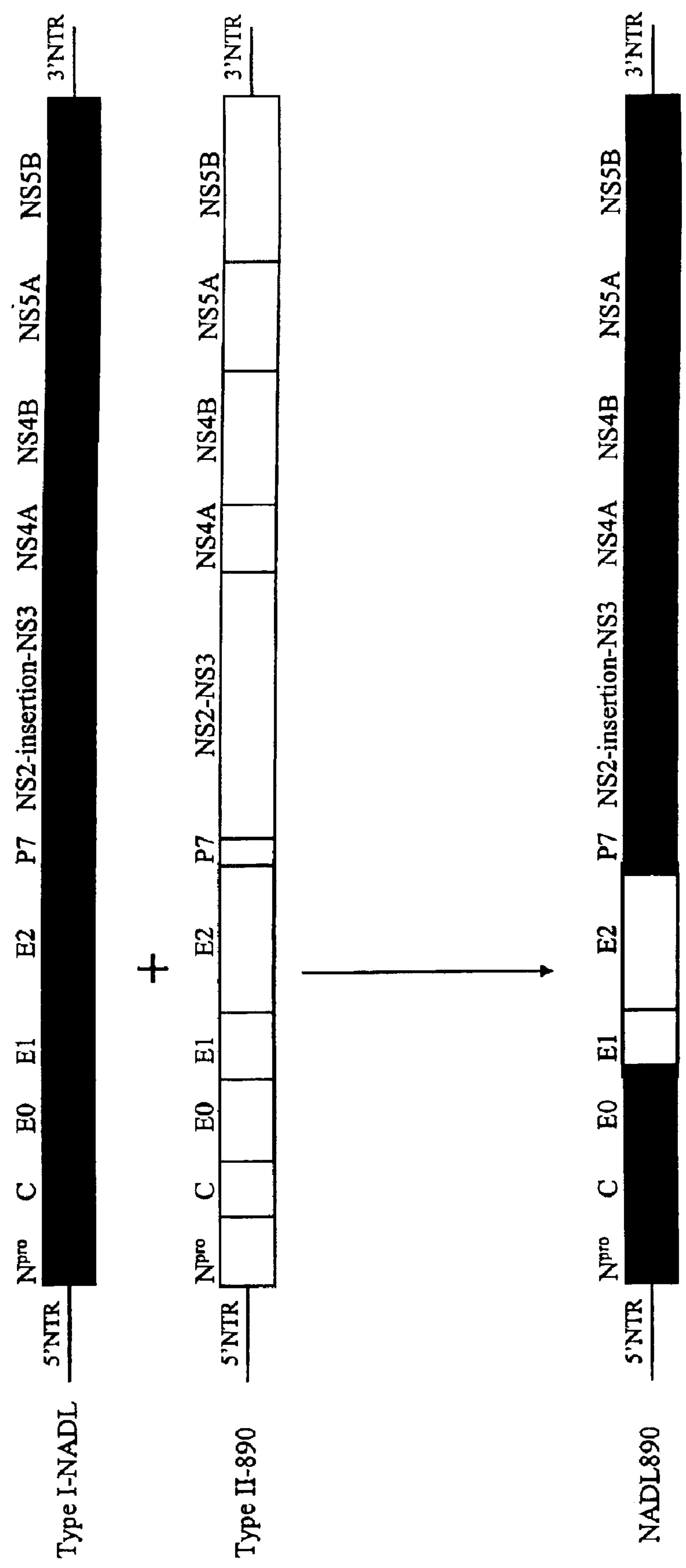
FIG. 1 provides schematic representations of the genomes of NADL (type I BVDV), 890 (type II BVDV) and NADL890 (hybrid virus).

One embodiment of the present invention provides genetically engineered type I/type II hybrid BVD viruses having a hybrid genome derived by substituting a portion of the genome of a type I BVD virus with the corresponding portion of the genome of a type II BVD virus.

BVD "viruses", "viral isolates" or "viral strains" as used herein refer to BVD viruses that consist of the viral genome, associated proteins, and other chemical constituents (such as lipids). Ordinarily, the BVD virus has a genome in the form of RNA. RNA can be reverse-transcribed into DNA for use in cloning. Thus, references made herein to nucleic acid and BVD viral sequences encompass both viral RNA sequences and DNA sequences derived from the viral RNA sequences. For convenience, genomic sequences of BVD as depicted in the SEQUENCE LISTING hereinbelow only refer to the DNA sequences. The corresponding RNA sequence for each is readily apparent to those of skill in the art.

The BVDV genome is approximately 12.5 kb in length and contains a single open reading frame located between the 5' and 3' NTRs. The viral proteins encoded by the open reading frame for both type I and type II BVDV are, from 5' to 3', $N^{pro}$, C, E0, E1, E2, p7, NS2, NS3, NS4A, NS4B, NS5A, and NS5B. A polyprotein of approximately 438 kD is first translated from the open reading frame and is processed into viral structural and nonstructural proteins via cellular and viral protease.

"A type I/type II hybrid virus" or simply "a hybrid virus" as used herein refers to a virus carrying a hybrid genome, i.e., a genome of a type I BVD virus wherein a portion of the type I genome is replaced with the corresponding portion of the genome of a type II BVD virus.

Preferably, the hybrid viruses of the present invention carry a genome of a type I BVD virus wherein at least a portion of "the E1–E2 region" of the type I genome is replaced with the corresponding portion of the E1–E2 region of a type II BDV virus.

By "at least a portion of the E1–E2 region" is meant at least a portion of the E1-encoding sequence, or at least a portion of the E2-encoding sequence, or combinations thereof.

A number of type I and type II BVD viruses are known to those skilled in the art and are available through, e.g., the American Type Culture Collection. The genomic nucleic acid molecules of these type I and type II BVD viruses can be isolated for making a type I/type II hybrid virus of the present invention.

In accordance with the present invention, a preferred choice of a type I virus is NADL (VR-534) and a preferred choice of a type II virus is 890.

A most preferred hybrid BVD virus of the present invention is NADL890. NADL890 has been generated as described in the Examples section below. Although this procedure can be used to obtain the virus, a plasmid containing the complete NADL890 genomic sequence, designated as pNADL890 (SEQ ID NO: 9 and FIG. 3) has been deposited with the American Type Culture Collection (ATCC #PTA-3098) and represents the preferred source for isolating NADL890. Standard procedures can be used to propagate and purify the plasmid. The preferred prokaryotic host cell for plasmid propagation is *E. coli* GM2163 cell line, but some other cell types can also be used. RNA transcribed from the plasmid can be introduced by transfection into eukaryotic host cells capable of supporting virus production, such as MDBK cells. The virus can be produced in such host cells and isolated therefrom in highly purified form using known separation techniques such as sucrose gradient centrifugation.

The present invention also encompasses hybrid viruses having a genomic sequence substantially the same as SEQ ID NO: 10. Sequences that are substantially the same as SEQ ID NO: 10 may include, for example, degenerate nucleic acid sequences that encode the same BVD proteins as SEQ ID NO: 10, or sequences made by introducing into SEQ ID NO: 10, one or more insubstantial additions or substitutions. In particular, sequences carrying mutations or containing alterations that do not substantially alter the characteristics of NADL890 with respect to infectivity and antigenicity fall within the scope of the invention. Such mutations or alterations should exhibit at least 30% homology to SEQ ID NO: 10. Preferably, such mutations or alterations should exhibit at least about 60% homology, and more preferably at least 90% homology, and even more preferably about 95% homology to SEQ ID NO: 10. The methods for introducing mutations into a given sequence are well known in the art.

Another embodiment of the present invention is directed to isolated genomic nucleic molecules of the hybrid BVD viruses as described above. Nucleic acid molecules as used herein encompass both RNA and DNA.

In this embodiment, the isolated genomic nucleic molecule of a hybrid BVD virus contains a genomic sequence of a type I virus wherein at least a portion of the E1–E2 region of the type I genomic sequence is replaced with the corresponding portion of the E1–E2 region of a type II virus.

A preferred nucleic acid molecule of the present invention is SEQ ID NO: 10, setting forth the genomic sequence of the hybrid virus NADL890. Nucleic acid molecules having substantially the same sequence as SEQ ID NO: 10 are also encompassed by the present invention.

In another embodiment, the present invention provides vectors in which the genomic nucleic acid sequence of a hybrid BVD virus as described herein above has been incorporated. Such vectors can be introduced into appropriate host cells, either for the production of large amounts of the genomic nucleic acid molecules or for the production of progeny hybrid BVD viruses. The vectors may contain other sequence elements to facilitate vector propagation, isolation and subcloning; for example, selectable marker genes and origins of replication that allow for propagation and selection in bacteria and host cells. A particularly preferred vector of the present invention is pNADL890 (SEQ ID NO: 9) (ATCC #PTA-3098), in which the genomic sequence of NADL890 (SEQ ID NO: 10) has been inserted.

Still another embodiment of the present invention is directed to host cells into which the genomic nucleic acid molecule of a hybrid BVD virus of the present invention has been introduced. "Host cells" as used herein include any prokaryotic cells transformed with the genomic nucleic acid molecule, preferably provided by an appropriate vector, of a hybrid BVD virus. "Host cells" as used herein also include any eukaryotic cells infected with a hybrid BVD virus or otherwise carrying the genomic nucleic acid molecule of a hybrid BDV virus. A preferred prokaryotic host cell for plasmid propagation is *E. coli* GM2163 cell line, but other cell types can also be used. Preferred eukaryotic host cells include mammalian cells such as MDBK cells (ATCC CCL 22). However, other cultured cells can be used as well. The invention further includes progeny virus produced in such host cells.

In a further aspect of the invention, the type I/type II hybrid BVD viruses of the present invention, as well as the genomic nucleic acid molecules of such viruses are used in compositions and methods for treating infections caused by type I or type II BVDV, or a combination of type I and type II BVDV.

In one embodiment, the present invention provides immunogenic compositions in which one or more of the hybrid BVD viruses described above have been included.

By "immunogenic" is meant the capacity of a hybrid BVD virus in provoking an immune response in an animal against type I or type II BVD viruses, or against both type I and type II BVD viruses. The immune response can be a cellular immune response mediated primarily by cytotoxic T-cells, or a humoral immune response mediated primarily by helper T-cells, which in turn activates B-cells leading to antibody production.

According to the present invention, the viruses are preferably attenuated by chemical inactivation or by serial passages in cell culture prior to use in an immunogenic composition. The methods of attenuation are well known to those skilled in the art.

A preferred hybrid virus to be included in an immunogenic composition of the present invention is NADL890. As the parent virus NADL is an attenuated BVD strain, further attenuation of NADL890 is preferred, although not required, before its use in an immunogenic composition.

In an alternative embodiment, the immunogenic compositions of the present invention include a genomic nucleic acid molecule of the hybrid virus NADL890.

The immunogenic compositions of the present invention can also include additional active ingredient such as other immunogenic compositions against BVDV, e.g., those described in copending U.S. patent application Ser. No. 08/107,908, WO 9512682, WO 9955366, U.S. Pat. Nos. 6,060,457, 6,015,795, 6,001,613, and 5,593,873, all of which are incorporated by reference in their entirety.

In addition, the immunogenic compositions of the present invention can include one or more veterinarily-acceptable carriers. As used herein, "a veterinarily-acceptable carrier" includes any and all solvents, dispersion media, coatings, adjuvants, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others. Stabilizers include albumin, among others. Adjuvants include, but are not limited to, the RIBI adjuvant system (Ribi inc.), alum, aluminum hydroxide gel, oil-in water emulsions, water-in-oil emulsions such as, e.g., Freund's complete and incomplete adjuvants, Block co polymer (CytRx, Atlanta Ga.), SAF-M (Chiron, Emeryville Calif.), AMPHIGEN® adjuvant, saponin, Quil A, QS-21 (Cambridge Biotech Inc., Cambridge Mass.), or other saponin fractions, monophosphoryl lipid A, Avridine lipid-amine adjuvant, heat-labile enterotoxin from *E. coli* (recombinant or otherwise), cholera toxin, or muramyl dipeptide, among many others. The immunogenic compositions can further include one or more other immunomodulatory agents such as, e.g., interleukins, interferons, or other cytokines.

The immunogenic compositions of the present invention can be made in various forms depending upon the route of administration. For example, the immunogenic compositions can be made in the form of sterile aqueous solutions or dispersions suitable for injectable use, or made in lyophilized forms using freeze-drying techniques. Lyophilized immunogenic compositions are typically maintained at about 4° C., and can be reconstituted in a stabilizing solution, e.g., saline or and HEPES, with or without adjuvant.

The immunogenic compositions of the present invention can be administered to animal subjects to induce an immune response against type I or type II BVD viruses, or against both type I and type II BVD viruses. Accordingly, another embodiment of the present invention provides methods of stimulating an immune response against type I or type II BVD viruses, or against a combination of type I and type II BVD viruses by administering to an animal subject an effective amount of an immunogenic composition of the present invention described above. By "animal subject" is meant to include any animal that is susceptible to BVDV infections, such as bovine, sheep and swine.

In accordance with the methods of the present invention, a preferred immunogenic composition for administration to an animal subject includes the hybrid virus NADL890. An immunogenic composition containing a hybrid virus, preferably attenuated by chemical inactivation or serial passage in culture, is administered to a cattle preferably via parenteral routes, although other routes of administration can be used as well, such as e.g., by oral, intranasal, intramuscular, intra-lymph node, intradermal, intraperitoneal, subcutaneous, rectal or vaginal administration, or by a combination of routes.

Immunization protocols can be optimized using procedures well known in the art. A single dose can be administered to animals, or, alternatively, two or more inoculations can take place with intervals of two to ten weeks. The extent and nature of the immune responses induced in the cattle can be assessed by using a variety of techniques. For example, sera can be collected from the inoculated animals and tested for the presence of antibodies specific for BVD viruses, e.g., in a conventional virus neutralization assay. Detection of responding CTLs in lymphoid tissues can be achieved by assays such as T cell proliferation, as indicative of the induction of a cellular immune response. The relevant techniques are well described in the art, e.g., Coligan et al. *Current Protocols in Immunology*, John Wiley & Sons Inc. (1994).

Another aspect of the present invention is directed to vaccine compositions.

The term "vaccine" as used herein refers to a composition which prevents or reduces the risk of infection or which ameliorates the symptoms of infection. The protective effects of a vaccine composition against a pathogen are normally achieved by inducing in the subject an immune response, either a cell-mediated or a humoral immune response or a combination of both. Generally speaking, abolished or reduced incidences of BVDV infection, amelioration of the symptoms, or accelerated elimination of the viruses from the infected subjects are indicative of the protective effects of a vaccine composition. The vaccine compositions of the present invention provide protective effects against infections caused by either or both of type I and type II BVD viruses.

In one embodiment, the vaccine compositions of the present invention include an effective amount of one or more of the above-described hybrid BVD viruses, preferably NADL890. Purified NADL890 viruses can be used directly in a vaccine composition, or preferably, NADL890 viruses can be further attenuated by way of chemical inactivation or serial passages in vitro. Typically, a vaccine contains between about $1\times10^6$ and about $1\times10^8$ virus particles, with a veterinarily acceptable carrier, in a volume of between 0.5 and 5 ml. The precise amount of a virus in a vaccine composition effective to provide a protective effect can be determined by a skilled veterinary physician. Veterinarily acceptable carriers suitable for use in vaccine compositions can be any of those described hereinabove.

In another embodiment, the vaccine compositions of the present invention include the nucleic acid molecule of the hybrid virus NADL890. Either DNA or RNA molecules encoding the NADL890 genome can be used in vaccines. The DNA or RNA molecule can be present in a "naked" form or it can be administered together with an agent facilitating cellular uptake (e.g., liposomes or cationic lipids). The typical route of administration will be intramuscular injection of between about 0.1 and about 5 ml of vaccine. Total polynucleotide in the vaccine should generally be between about 0.1 μg/ml and about 5.0 mg/ml. Polynucleotides can be present as part of a suspension, solution or emulsion, but aqueous carriers are generally preferred. Vaccines and vaccination procedures that utilize nucleic acids (DNA or mRNA) have been well described in the art, e.g., U.S. Pat. Nos. 5,703,055, 5,580,859, 5,589,466, International Patent Publication WO 98/35562, and by Ramsay et al., 1997, *Immunol. Cell Biol.* 75:360–363; Davis, 1997, *Cur. Opinion Biotech.* 8: 635–640; Manickan et al., 1997, *Critical Rev. Immunol.* 17: 139–154; Robinson, 1997, *Vaccine* 15(8): 785–787; Robinson et al., 1996, *AIDS Res. Hum. Retr.* 12(5): 455–457; Lai and Bennett, 1998, *Critical Rev. Immunol.* 18:449–484; and Vogel and Sarver, 1995, *Clin. Microbiol. Rev.* 8(3): 406–410, all of which are incorporated herein by reference.

The vaccine compositions of the present invention can also include additional active ingredient such as other vaccine compositions against BVDV, e.g., those described in WO 9512682, WO 9955366, U.S. Pat. Nos. 6,060,457, 6,015,795, 6,001,613, and 5,593,873.

Vaccination can be accomplished by a single inoculation or through multiple inoculations. If desired, sera can be collected from the inoculated animals and tested for the presence of antibodies to BVD virus.

In another embodiment of the present invention, the above vaccine compositions of the present invention are used in treating BVDV infections. Accordingly, the present invention provides methods of treating infections in animal subjects caused by BDV viruses of type I or type II, or a combination of type I and type II, by administering to an animal, a therapeutically effective amount of a hybrid BVD virus of the present invention.

By "animal subjects" is meant to include any animal that is susceptible to BVDV infections, such as bovine, sheep and swine. By "treating" or "vaccinating" is meant preventing or reducing the risk of infection by a virulent strain of BVDV (either or both of Type I and Type II), ameliorating the symptoms of a BVDV infection, or accelerating the recovery from a BVDV infection.

Those skilled in the art can readily determine whether a genetically engineered hybrid virus needs to be attenuated before administration. A preferred hybrid virus of the present invention, NADL890, can be administered directly to an animal subject without additional attenuation. The amount of a virus that is therapeutically effective may vary depending on the particular virus used, the condition of the cattle and/or the degree of infection, and can be determined by a veterinary physician.

In practicing the present methods, a vaccine composition of the present invention is administered to a cattle preferably via parenteral routes, although other routes of administration can be used as well, such as e.g., by oral, intranasal, intramuscular, intra-lymph node, intradermal, intraperitoneal, subcutaneous, rectal or vaginal administration, or by a combination of routes. Boosting regiments may be required and the dosage regimen can be adjusted to provide optimal immunization.

A further aspect of the present invention provides methods of determining the attenuated virus of a prior vaccination as the origin of the BVD virus present in an animal subject.

The hybrid BVD viruses of the present invention are distinguished from wild type BVD strains in both the genomic composition and the proteins expressed. Such distinction allows discrimination between vaccinated and infected animals, and permits the identification of the BVDV in the event of alleged vaccine-associated outbreaks. For example, a determination can be made as to whether an animal tested positive for BVDV in certain laboratory tests carries a virulent or pathogenic BVD virus, or simply carries a hybrid BVD virus of the present invention previously inoculated through vaccination.

A variety of assays can be employed for making the determination. For example, the viruses can be isolated from the animal subject tested positive for BVDV, and nucleic acid-based assays can be used to determine the presence a indicative of a hybrid BVD virus used in a prior vaccination. The nucleic acid-based assays include Southern or Northern blot analysis, PCR, and sequencing. Alternatively, protein-based assays can be employed. In protein-based assays, cells or tissue suspected of an infection can be isolated from the animal tested positive for BVDV. Intracellular extracts can be made from such cells or tissues and can be subjected to, e.g., Western Blot, using appropriate antibodies against viral proteins that may distinctively identify the presence of the hybrid virus previously inoculated, as opposed to the presence of a type I BVD or type II BVD or a combination thereof. For example, if the hybrid virus NADL890 is used in a prior vaccination, such virus would be reactive to antibodies specific for E1–E2 of type II viruses, and would also be reactive to antibodies specific for type I viral proteins other than E1 and E2. Additionally, such hybrid virus would not be reactive to antibodies specific for E1–E2 of type I viruses, or to antibodies specific for type II proteins which are not E1 or E2. Any variations of the foregoing assays are also encompassed by the present invention.

In another embodiment, the present invention is directed to a method of modifying a genome of an isolated wild type BVD virus of type I in such a manner as to make it suitable for use in an immunogenic composition or a vaccine against both type I and type II BVD viruses.

According to this method of the present invention, the genomic nucleic acid of a type I BVD virus is modified such that a portion of the genome of the type I virus is replaced by the corresponding portion of the genome of a type II virus. Preferably, a portion of the E1–E2 region of the genome of a type I virus is replaced with the corresponding portion of the E1–E2 region of the genome of a type II virus. More preferably, the entire E1–E2 region of the genome of a type I virus is replaced with the entire E1–E2 region of the genome of a type II virus. These modifications to the genome of a wild type type I BVD virus can be made by following procedures well known in the art. The hybrid genome can be cloned into an appropriate vector and produced in large amounts. Either the hybrid genomic nucleic acid molecule or the vector comprising the hybrid genomic nucleotide sequence can be transformed or transfected into a host cell for the purpose of making either large amounts of hybrid viral nucleic acid or hybrid virus itself.

The present invention is further illustrated by, but by no means limited to, the following examples.

EXAMPLE 1

Construction of Plasmid pNADL890

A. RNA Purification from Cells Infected with Type II Virus 890

Monolayers of Bovine cells MDBK (a derivative of Madin Darby Kidney cells clone 6) were cultured in Opti-MEM (GibcoBRL) with 5% calf donor serum (Nova-tech), and inoculated with type II virus 890 (ncp) with MOI=1. At 24 hr post-infection, cells were washed twice with cold PBS buffer and lysed with Ultraspec™ RNA reagent. Total RNA (viral and cellular) was isolated using the Ultraspec™ RNA isolation system following the manufacture's protocol (Biotecx Lab, Inc.), and served as template for RT/PCR reaction.

B. Generation of RT/PCR Fragment and Chimeric PCR Fragment which Contained the E1–E2 Region of 890 Viral Genome and a Region of the NADL Viral Genome from the C-Terminal of E2 to the N-Terminal of NS2

1) RT/PCR: Viral RNA purified from 890 infected-cells was used as template. Oligonucleotides 890E1a(+) (5'-CCA TACTGCGATGTGGATCGGAAGATCGGTTACG-3', SEQ ID NO: 1) and 890NADLE2a(−) (5'-CCAAAGTACATATCTGCCACCCAACAAGGCGAC CACTGC-3', SEQ ID NO: 2) were used as primers. The 5' forward primer, oligo 890E1a(+) (SEQ ID NO: 1), was designed to hybridize to the viral genomic region encoding the N-terminal of E1. The nucleotides of oligo 890E1a (+) (SEQ ID NO: 1) were identical to those of the 890 genome except for four nucleotide changes (GA to AT at positions 11–12, and GA to TC at positions 18–19) which reference to the nucleatides of SEQ ID NO: 1 at these positions match the sequences of NADL genome and created a restriction enzyme BsaBI site. The 3' reverse primer, oligo 890NADLE2a(−) (SEQ ID NO: 2), was designed to hybridize to the viral genome region encoding the C-terminal of E2. Less than half of the 16 nucleotides at the 5' end of oligo 890NADLE2a(−) matched the nucleotides of the NADL genome, and more than half of the 23 nucleotides at the 3' end of this oligo matched those of the 890 genome. The RT/PCR reaction was performed using the Superscript™ One-STEP™ RT-PCR system following the manufacture's protocol. In order to facilate the yield and accuracy of the PCR fragment, polymerase PFU (Stratagene Inc.) and eLongase (GibcoBRL) were added into the RT/PCR mix at a concentration of 1 unit/50:1. The RT/PCR fragment produced was 1649 bp long ("fragment 1", FIG. 2) which included most of the E1 and E2 coding region of the 890 genome, except that two amino acids at the N-terminal of E1 and 20 amino acids at the C-terminal of E2 were not included.

2) PCR: Two steps of PCR were performed to generate a PCR fragment which included the E1–E2 region of 890, and which could be easily inserted into the NADL genome to replace the E1–E2 region of NADL.

Generation of First PCR Fragment: Primers NADL890E2a(+) and NADLNS 2a(−) were designed to generate the first PCR fragment which contained the coding sequences from C-terminal of E2 to C-terminal of NS2 of the NADL genome. The 5'-forward primer, oligo NADL890E2a(+) (5'-GTGGTCGCCTTGTTGG GTGGCAGATATGTACTTTGG-3', SEQ ID NO: 3) was designed to hybridize to the viral genome region encoding the C-terminal of E2. 12 nucleotides at the 5' end of oligo NADL890E2a(+) matched the nucleotides of the 890 genome and the rest of the nucleotides of this oligo matched the nucleotides of the NADL genome. The 3' reverse primer, Oligo NADLNS2a(−) (5'-CAGCCACG TCMCCTTCCACCTCG-3', SEQ ID NO: 4), was designed to hybridize to the middle of the NS2 coding region at position 4185–4208 (the numbering was based on the nucleotide numbering of the NADL genome). Plasmid pNADLp15a, derived from plasmid pvvNADL (Vassilev et al., *J. Virol.* 71: 471–478, 1997) was used as template. PCR amplification was performed using primers at a final concentration of 0.5 uM each, 10 ng of plasmid pNADLp15a DNA, and 2.5 units of Pfu DNA polymerase (Stratagene, La Jolla, Calif.). Twenty five cycles of amplification were performed under the following conditions: denaturation at 94° C. for 30 seconds, annealing at 45° C. for 45 seconds, and extension at 72° C. for two minutes. The PCR product ("fragment 2", FIG. 2) was 705 bp long.

Generation of Final PCR Fragment: The final PCR fragment was generated using primers 890E1a(+) (SEQ ID NO: 1) and NADLNS2a(−) (SEQ ID NO: 4). The PCR reaction were performed with primers at the final concentration of 0.5 uM, fragment 1 and fragment 2 as templates (10 ng DNA of each), 2.5 units of Pfu DNA polymerase (Stratagene, La Jolla, Calif.) and 1 unit of eLongase (GibcoBRL). Thirty cycles of amplification were performed with three steps for each cycle: denaturation at 94° C. for 30 seconds; annealing at 45° C. for 45 seconds; and extension at 72° C. for 5 minutes. The PCR product ("fragment 3", FIG. 2) was 2319 bp long and contained one BsaBI site at the 5'-end and one MfeI site at the 3'-end.

C. Cloning of Construct pNADL890.

Figure 2:
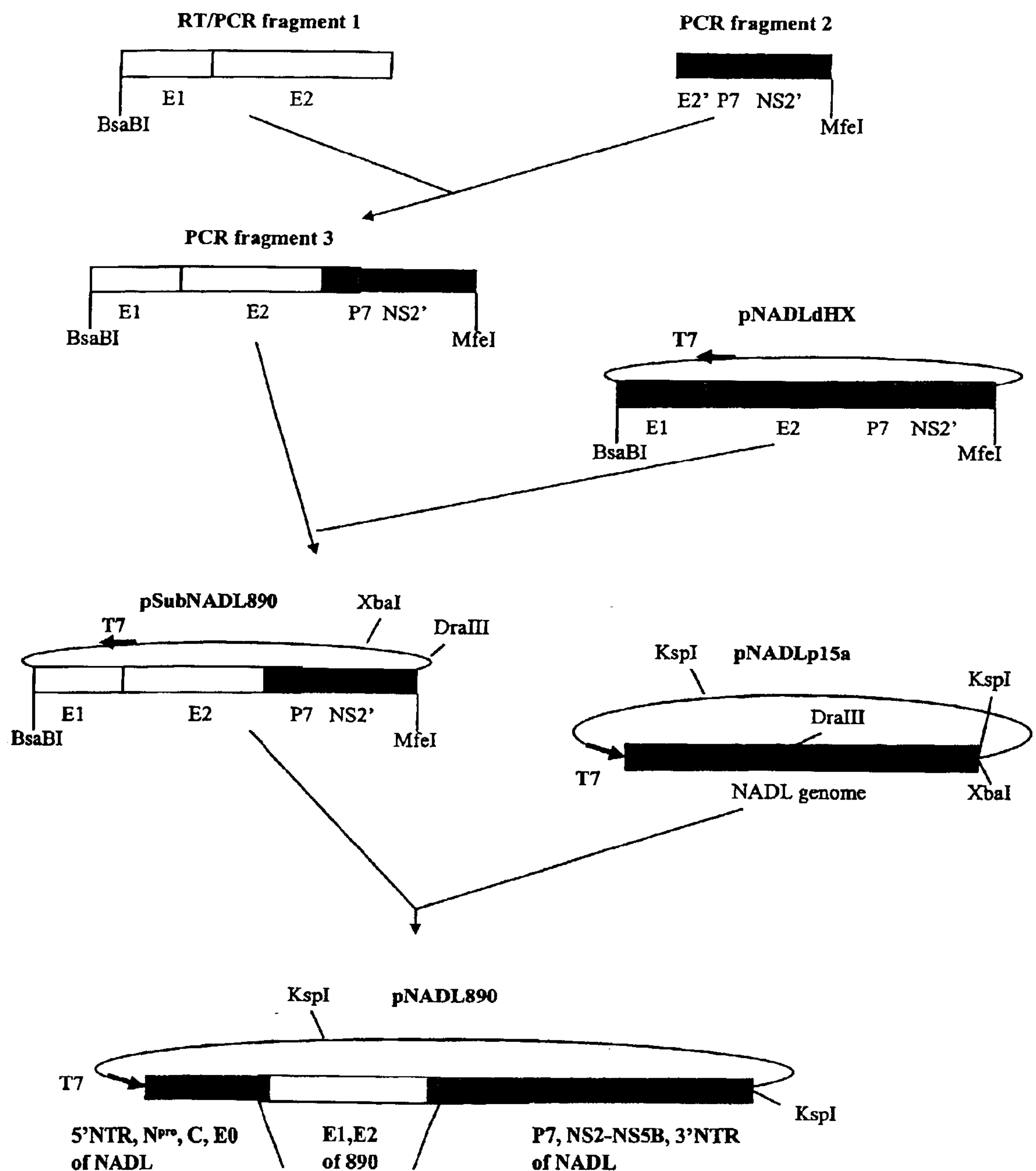
FIG. 2 graphically depicts the steps of constructing plasmid pNADL890.

1) Generation of Subclone pBVDdHX: Genetic modification in the envelope region was found to be difficult in the full-length clone. To overcome this problem, a smaller plasmid was constructed as follows in order to replace the envelope region of BVDV. plasmid DNA pNADLp15a (0.1 ug) was first digested with restriction enzymes HpaI (at nucleotide position 5791 in the NADL genome) and XbaI (at nucleotide position 12584 in the NADL genome), then end-filled with 2 units of polymerase Klenow (Boehringer Mannheim) and 0.5 mM dNTPs. After agarose-gel purification and elution with Geneclean (Bio101, Vista, Calif.) glassmilk, the fragment of 9926 bp in size was ligated with T4 DNA ligase (NEB). *E. coli* strain GM2163 (NEB) was transformed with an aliquot of the ligation mixture by way of electroporation. The desired DNA clone ("pBVDdHX"), identified from the transformants, was used as a vector for further cloning (FIG. 2).

2) Generation of Subclone pSubNADL890: PCR fragment 3 was digested with restriction enzymes BsaBI and MfeI, agarose-gel purified and eluted with Geneclean glassmilk, then inserted into the BsaBI/MfeI sites in vector plasmid pBVDdHX. *E. coli* strain GM2163 (NEB) was transformed by way of electroporation. The desired DNA clone ("pSubNADL890"), identified from the transformants, contained the E1–E2 region of 890 genome, and was used for further cloning (FIG. 2).

3) Generation of Final Construct pNADL890: After digested with restriction enzymes DraIII (at nucleotide position 5222 in the NADL genome) and XbaI, plasmid DNA pNADLp15a released a DNA fragment with the size of 7400 bp. The 7400-bp fragment was inserted into the DraIII/XbaI sites of plasmid pSubNADL890 to generate plasmid pNADL890. pNADL890 contained a hybrid BVDV genomic sequence, i.e., the E1–E2 portion was from the 890 genome and the remaining portion was from NADL (see FIGS. 1 and 2). pNADL890 was 16713 bp long and contained a coding region of 12572 bp (FIG. 3, the first nucleotide of viral genome is position 1).

EXAMPLE 2

Characterization of the Type I/Type II Hybrid Virus (NADL890 Virus)

In Vitro Transcription and RNA Transfection

RNA transcripts were synthesized in vitro using T7 RNA polymerase and MEGAscript™ reagent (Ambion) according to the manufacture's protocol. Plasmid DNAs carrying a BVDV genomic sequence were linearized with Ksp I and treated with T4 DNA polymerase to remove the 3' overhang. Transcription reaction products were analyzed by gel electrophoresis. 1 to 5 μg of transcript RNA was added to 200 μl of Opti-MEM (GibcoBRL) containing 6 μg of Lipofectin (Gibco-BRL). RNA/Lipids samples were incubated for 10 to 15 min at room temperature. During this time, monolayers (50 to 60% confluent) of MDBK (a derivative of Madin Darby Kidney cell clone 6) grown in six-well plates (35 mm diameter) were washed twice with RNase-free PBS and once with Opti-MEM. After the final wash was removed, the transfection mixtures were added to each cell wells, and the samples were incubated for 10 min at room temperature with gently rocking. 1-ml Opti-MEM was then added to the wells and the samples were incubated for another three hours at 37° C. A 3-ml volume of Opti-MEM containing 2–3% bovine donor calf serum (CDS) was added to each well. Following incubation for two to four days at 37° C., one set of the duplicated cells were fixed with 80% acetone and analysed with immunohistochemistry assay to visualize the BVDV plaques. Another set of the cells were collected for preparing virus stocks and for further analysis.

Infectivity of the Clone pNADL890

RNAs were synthesized in vitro from pNADL890 and pNADLp15A (positive control), respectively, as described above. Monolayers of MDBK cells were transfected with RNA using Lipofectin. At 24 and 48 hr post-transfection, one set of total transfected cell monolayers were collected to reinfect fresh MDBK monolayers for generating virus stocks; and another duplicate set of the transfected cell monolayers were fixed with 80% acetone for immunohistochemistry assay. Immunohistochemistry assays were conducted using a Vectastain Elite ABC kit (Vector laboratories) by following the manufacturer's instructions. Monoclonal antibodies used for BVD viral protein detection were 15C5 (specific for E0) and 20.10.6 (specific for NS3) at 1:1000 dilution. Viruses (or "NADL890 viruses") were recovered from cells transfected with RNA derived from pNADL890 at a rate nearly as fast as from cells transfected with RNA derived from pNADLp15A. At 24 hr post-transfection with RNA derived from either pNADLp15A or pBVDdN6, envelop protein E0 and protease NS3 were detected; and viruses were also recovered from the transfected cells.

Phenotype Analysis of NADL890 Virus

Figure 4:
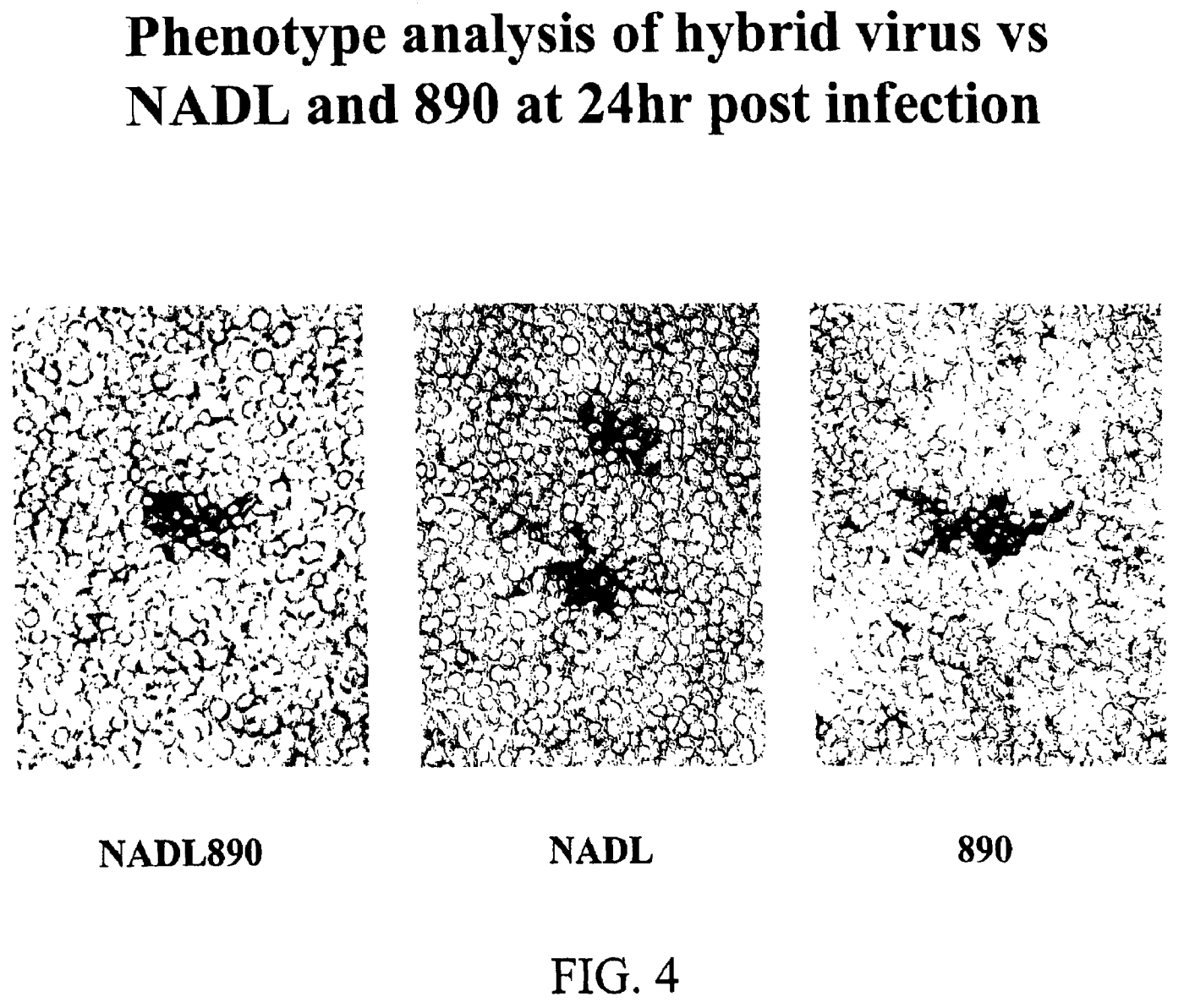

In order to characterize the rescued NADL890 viruses, early passage virus stocks (passage 2) were inoculated onto MDBK cell monolayers. For comparison, MDBK cell monolayers were also inoculated with wild type NADL viruses and 890 viruses, respectively. At specified post-infection times (16, 24, 32 and 48 hrs), the cell monolayers were fixed with 80% acetone. The infected cells were detected by an immunohistochemistry assay using monoclonal antibody 15C5 (specific for E0) at 1:1000 dilution and were examined with microscope. All three viruses were detectable as early as 16 hrs post-infection, and all formed big plaques at 24 hrs post infection (FIG. 4). NADL890 viruses grew as well as either of the parent viruses NADL or 890, but had cytopathic effects on cells in the same manner as NADL.

Genotype Analysis

The genome sequence of the rescued NADL890 viruses was examined to confirm the replacement of the E1–E2 region of the NADL genome with the E1–E2 region of the 890 genome. Viral RNAs of NADL890 (passage 3) were purified from infected MDBK monolayers using Ultraspec™ RNA reagent (Biotect) following the manufacturer's instruction. MDBK is a stably transformed bovine testis cell line which grow in Opti-MEM medium with 5% fetal equine serum (FES). RT/PCR was performed using Superscript™ One-STEP™ RT-PCR system following manufacture's protocol with primers NADLC5(+) and NADLp7(−). NADLC5(+) (5'-CAGAAACCCGACAGACTAGAAAGG-3', SEQ ID NO: 5) was the 5' forward primer, designed to hybridize to nucleotides 929–952 of pNADL890 which coded for the N-terminal of the C protein. NADLp7(−) (5'-GTACAGCAGCMGMGTATGTCACC-3', SEQ ID NO: 6) was the 3' reverse primer, designed to hybridize to nucleotides 3643–3667 of pNADL890 which located at the middle of the coding region of p7. In order to facilitate the yield of the PCR fragment, eLongase (GibcoBRL) was added into the RT/PCR mix at a concentration of 1 unit/50:l. The RT/PCR fragment was 2738 bp long, and the sequence of the fragment was examined by DNA sequence analysis using 5' forward primers Seq2(+) (SEQ ID NO: 7) and NADLE06(+) (SEQ ID NO: 8) as well as a 3' reverse primer 890NADLE2a(−) (SEQ ID NO: 2). Seq2(+) (5'-GGAGCATACGCTGCTTCCCC-3', SEQ ID NO: 7) was designed to hybridize to nucleotides position 1865–1884 of pNADL890 which were located at the junction between the coding sequence for E0 and the coding sequence of E1. NADLE06(+) (5'-CGCCATGAGTGGAACAAGC-3', SEQ ID NO: 8) was designed to hybridize to nucleotides 1412–1430 of pNADL890 which were located at the middle of the coding sequence of E0.

Antigenicity of NADL890 Virus (1) Monoclonal antibody (mAb) recognition assay—Two mAbs, CA3 and CA34, recognized E2 protein from type I BVD viruses only. mAb C06007 recognized E2 protein from type II BVD viruses only. mAb 15C5 was specific to E0 protein and mAb 20.10.6 was specific to NS3 protein. Both 15C5 and 20.10.6 recognized the corresponding proteins from BVD viruses of either type I and or type II. Viruses NADL (type I), 890 (type II) and NADL890 (hybrid) were used to infect MDBK monolayers with MOI 1 for 24 and 48 hrs. Cell monolayers were fixed with 80% acetone and were subjected to immunohistochemistry staining was performed using the above five mAbs (1:1000 dilution). The results are summarized in table 1. All three viruses shown positive reaction (marked as +) to mAbs 15C5 and 20.10.6 with different intensity (++++ verses +++). Type I NADL viruses were reactive to mAbs CA3 and CA34, but not to mAb C06007. Type II 890 viruses and hybrid NADL890 viruses were not reactive to mAbs CA3 and CA34, but reactive to mAb C06007. These results indicate that the hybrid virus NADL890 in cell culture bears a type II antigenicity based on the E2 specificity.

TABLE I

Antigenicity of Virus NADL890 in Cell Culture

| mAb | Viruses: NADL (Type I) | 890 (Type II) | NADL890 (hybrid) |
|---|---|---|---|
| 15C5 | ++++ | ++++ | ++++ |
| 20.10.6 | +++ | +++ | +++ |
| C06007 | — | ++++ | ++++ |
| CA3 | ++++ | — | — |
| CA34 | +++ | +/− | +/− |

Figure 5:
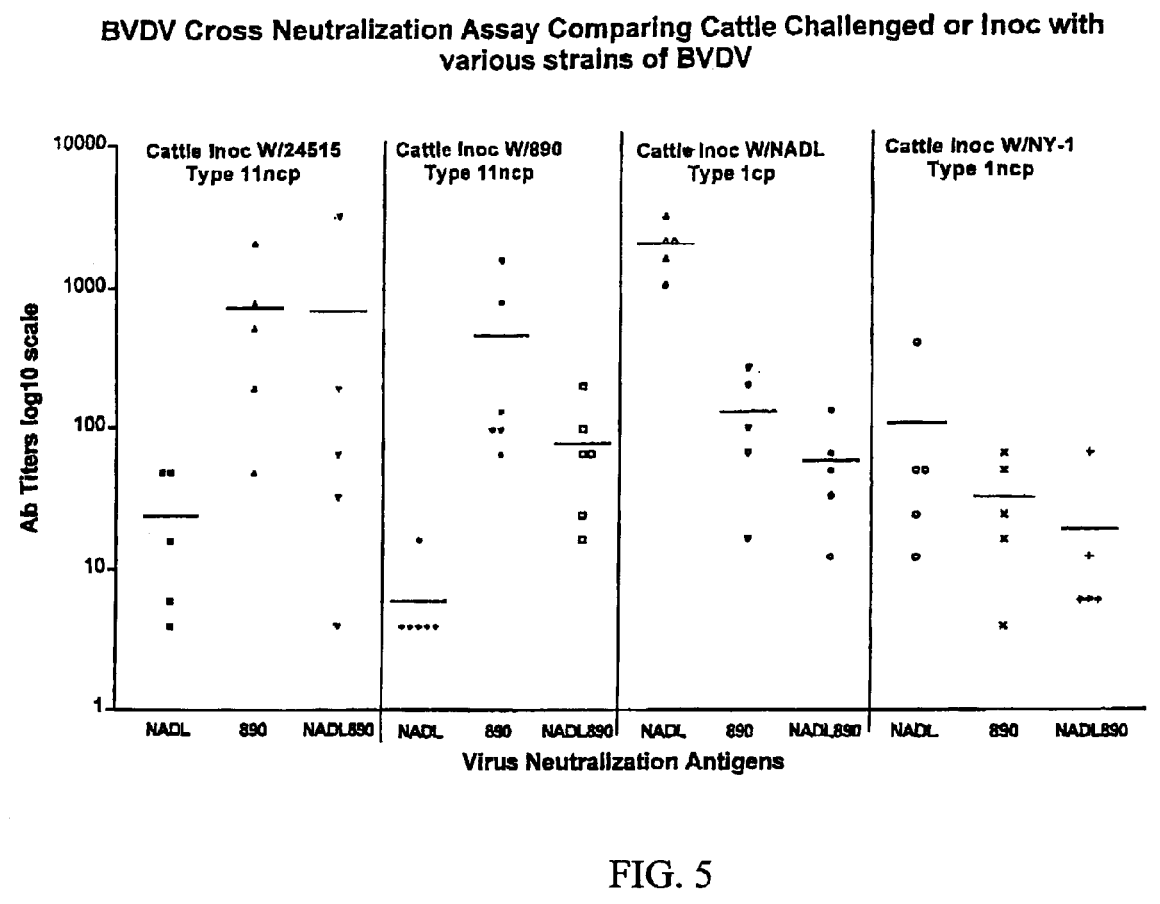

(2) Neutralization assay against BVDV infected cattle serum—Further analysis of virus NADL890 was performed in neutralization assays. Virus neutralization (VN) antigens included the hybrid virus NADL890, control virus NADL (type I) or control virus 890 (type II). Serum collected from cattle infected with type I viruses NADL (cp) and NY-1 (ncp), and serum collected from cattle infected with type II viruses 24515 (ncp) and 890 (ncp), were used in the neutralization assay. There were five cattle in each infected virus group. VN antigens (viruses NADL, 890 or NADL890) were incubated with cattle serum at different dilution (1:4, 1:8 and so on) at 37° C. for 1 hr, then were inoculated onto BT2 cells (ATCC, derived from bovine turbinate) for viability test using an immunoperoxidase assay. The procedure of the immunoperoxidase assay was similar to that of the immunohistochemistry assay described above, except that polyclonal goat-anti-BVDV serum was used for virus detection. Titers of serum antibodies reactive to each VN antigen are summarized in FIG. 5. The results demonstrate that type I virus NADL is more reactive to serum from cattle infected with type I viruses (NADL and NY-1), and that type II virus 890 and the hybrid virus are more reactive to serum of cattle infected with type II viruses (24515 and 890). This data confirms that the hybrid virus NADL890 bears type II antigenicity.

What is claimed is:

1. A hybrid BVD virus comprising a genome generated by substituting a portion of the genome of a type I BVD virus which comprises the E1–E2 region, with the corresponding portion of the genome of a type II BVD virus.

2. The hybrid BVD virus of claim 1, wherein said hybrid virus has the designation NADL890, the genome of which is set forth in SEQ ID NO: 10.

3. An immunogenic composition comprising the hybrid BVD virus of claim 1 or 2 and a veterinarily-acceptable carrier, wherein said hybrid BVD virus is attenuated.

4. A method of inducing an immune response against BVDV in an animal subject, comprising administering an immunologically effective amount of the hybrid BVD virus of claim 1 or 2 and a veterinarily-acceptable carrier.

5. The method of claim 4, wherein said immune response is a cellular or humoral immune response.

6. A vaccine composition comprising the hybrid BVD virus of claim 1 or 2 and a veterinarily-acceptable carrier, wherein said hybrid BVD virus is attenuated.

7. A method of treating a BVDV infection in an animal, comprising administering to said animal, a therapeutically effective amount of the hybrid BVD virus of claim 1 or 2.

* * * * *